(12) United States Patent  
Carlson

(10) Patent No.: US 6,299,449 B1
(45) Date of Patent: Oct. 9, 2001

(54) IMMEDIATE, LAMINATED, LIGHT-CURED DIRECT MULTI-COMPOSITE BRIDGE

(76) Inventor: Ronald Stanley Carlson, 4211 Waialae Ave. Ste 400, Honolulu, HI (US) 96816

(*) Notice: Subject to any disclaimer, the term of this patent is extended or adjusted under 35 U.S.C. 154(b) by 0 days.

(21) Appl. No.: 09/349,375

(22) Filed: Jul. 7, 1999

Related U.S. Application Data

(63) Continuation-in-part of application No. 08/545,372, filed on Jan. 11, 1996, now abandoned, and a continuation-in-part of application No. 08/929,144, filed on Sep. 10, 1997, now Pat. No. 5,984,682.

(51) Int. Cl.[7] .................................................. A61C 13/12
(52) U.S. Cl. .......................................... 433/180; 433/181
(58) Field of Search ................................... 433/162, 172, 433/180, 181, 215

(56) References Cited

U.S. PATENT DOCUMENTS 5,171,147 * 12/1992 Burgess ................................ 433/180
5,194,001 *  3/1993 Salvo .................................... 433/180

* cited by examiner

Primary Examiner—John J. Wilson

(57) ABSTRACT

A permanent dental bridge comprised entirely of one or more types of dental composite material may be constructed directly, i.e., without laboratory assistance, either in situ or ex situ, without reduction of the abutment teeth. The direct composite bridge comprises one or more composite pontics, integrally laminated attachment portions and substructure, and optional embedded reinforcement materials. In the in situ process, composite material is applied between abutment teeth in the patient's mouth, attachment portions are formed from the composite material, those attachment portions respectively attaching to corresponding surfaces on the abutment teeth, and the composite material is cured. The steps of application and curing of composite material are successively repeated until a completed dental bridge, including a pontic portion, is formed entirely within the patient's mouth. The ex situ process is accomplished by fabricating a composite pontic, applying composite material between the patient's abutment teeth, curing the composite material, applying a lamination of additional composite material between the abutment teeth, inserting the composite pontic into the lamination, and curing the lamination. In either process, a gingival stent can be utilized to act as a platform upon which the successive composite laminations may be formed and also, if employed immediately following tooth extraction, to act as a bandage. The stent is inserted into the patient's mouth before application of composite material between the abutment teeth, and is removed after formation of the completed bridge but prior to the contouring and finishing thereof. In either process, one or more reinforcement materials (including different types of dental composite) may be introduced in laminations between the abutment teeth for reinforcement.

20 Claims, 14 Drawing Sheets

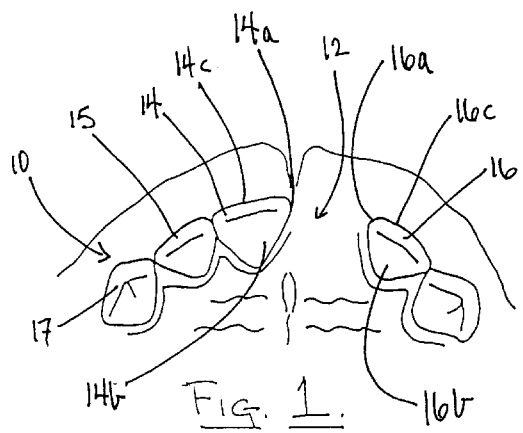
FIG. 1.
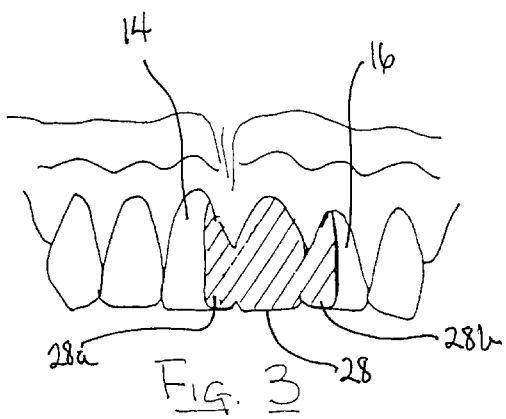
FIG. 3
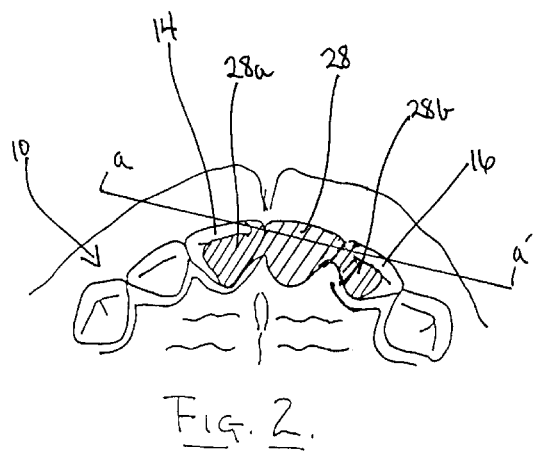
FIG. 2.
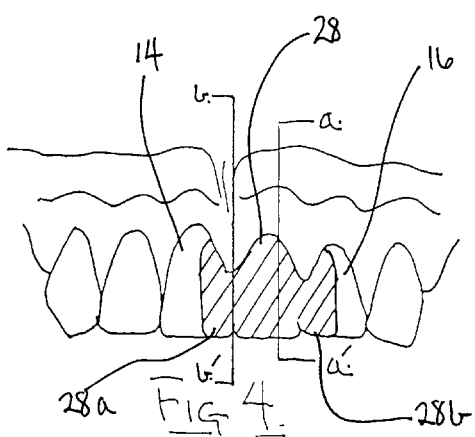
FIG. 4.
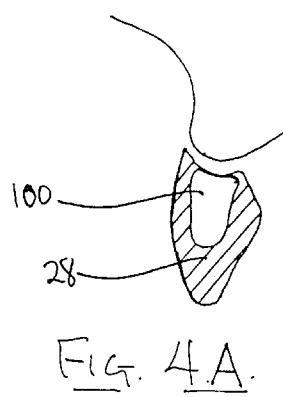
FIG. 4.A.
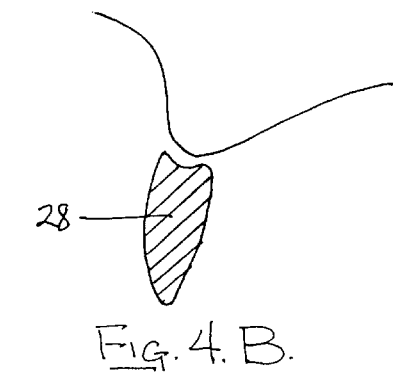
FIG. 4.B.

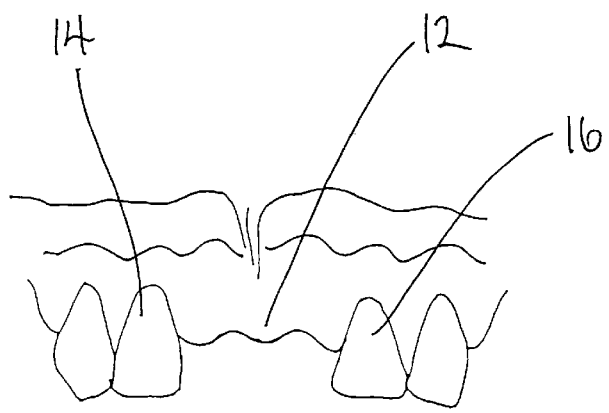
FIG. 16.
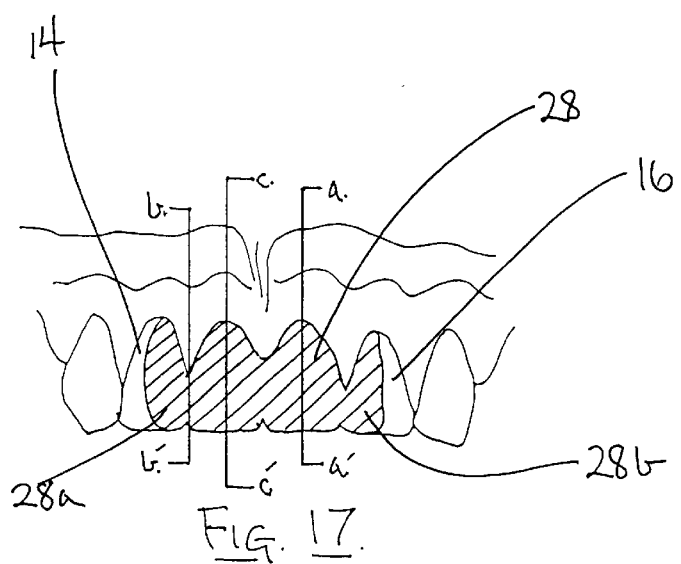
FIG. 17.
FIG. 17.A.          FIG. 17.B.

IMMEDIATE, LAMINATED, LIGHT-CURED DIRECT MULTI-COMPOSITE BRIDGE

CROSS-REFERENCE TO RELATED APPLICATIONS

This application is a continuation-in-part of application Ser. No. 08/545,372, filed Jan. 11, 1996, now abandoned, and of application Ser. No. 08/929,144, filed Sep. 10, 1997, now U.S. Pat. No. 5,984,682.

BACKGROUND OF THE INVENTION

1. Field of the Invention

The invention is concerned with, generally, the domain of restorative and prosthetic dentistry, specifically, "fixed partial dentures," more commonly known as "fixed dental bridgework." The traditional or "indirect" method of producing fixed dental bridgework typically involves the extra-oral, or outside the patient's mouth, use of molds, metal frameworks, and pressurized ovens to produce bridgework. The "direct" method of producing fixed dental bridgework is done in situ, intraorally, entirely within the patient's mouth using particle-filled dental restorative resin (called "dental composite" or simply "composite"), and plain dental restorative resin, without reduction of the abutment teeth or the use of cement or luting agents.

2. Description of Related Art

Fixed dental bridgework has traditionally involved the following process: (1) during the first office visit by the patient, the dentist surgically reduces the anchor or "abutment" teeth on either side of a space (edentulous area) in a dental arch to be spanned by the bridgework; (2) the dentist makes an impression of the reduced abutment teeth and edentulous area; (3) the impression is sent to a laboratory for construction of a model to which the bridgework is conformed during fabrication; (4) metal "pontic" castings, a metal framework that holds the pontics (artificial teeth), and attachment wings are fabricated; (5) in a special high temperature oven, porcelain may then be fused to the pontic forms, and to the metal attachment wings on each end of the metal bridge framework if desired, depending on the original bridgework design; (6) the bridgework is sent from the laboratory to the dentist, (7) during a second office visit by the patient, the dentist inserts and adjusts the bridgework in the patient's mouth; and (8) the dentist "permanently" cements the attachment wings or crowns on the ends of the bridgework to abutment teeth to fix the bridgework in place. Examples lo of the type of bridgework described above are shown in U.S. Pat. No. 5,194,001 to Salvo and in U.S. Pat. No. 5,000,687 to Yarovesky, et al.

A poor fit between the traditional bridgework and the abutment teeth cannot be discovered until the finished bridgework is inserted into the patient's mouth; a poor fit sometimes develops after a period of wear. To cure a poor fit, the bridgework must be removed from the patient's mouth, modified, then reattached. Sometimes, several iterations of attachment, removal, modification, reattachment are necessary, each requiring an office visit by the patient. Attachment wings or crowns run the range of mechanical and/or adhesive devices, such as screws, foils, films, screens, mastics, hooks, etc. Frequently, the reduction and/or process of attachment (especially the use of screws) injures the abutment teeth and can lead to caries, abscesses, and/or tooth death. Removal of the bridgework after cementation of the attachment wings to the abutment teeth sometimes injures the abutment teeth, or even requires their removal.

For decades there has been a quest for a more efficient, effective, and non-invasive means of replacing missing teeth in a fixed manner. Extraordinary efforts have been devoted to trying to devise methods that do not require cutting or otherwise mutilating the abutment teeth. Two of the most common methods devised to avoid reducing the abutment teeth are well known as the "Maryland bridge" and the "Rochette bridge." The Maryland bridge and the Rochette bridge are constructed with a metal framework of nickel-chromium and beryllium in a laboratory, etched with an acid medium or sandblasted on the tissue side surface of the attachment hooks, and then cemented to the natural abutment teeth with a polymer luting agent. Due to the inflexibility of the metal frame and the weak bond of the polymer to metal and polymer to teeth, the attachment hooks can separate from the abutment teeth. There are additional serious disadvantages with the Maryland and Rochette bridges, as well as with other indirect bridgework. In the area of aesthetics, the underlying metal may "shine-through" the pontic surface, disrupting the color, hue, value and shade of the replacement tooth. The high-fusing-porcelain can rapidly abrade natural teeth opposite the bridge. The metallic content of the metal bridges sometimes precipitates allergic or even less understood impairment of the patient's health. There is a growing and real concern for the quality and quantity of metal used in dentistry and the deleterious effects on the bio-environment of the oral cavity. All three kinds of metals utilized in the previously mentioned bridges are bio-toxic to some degree. Nickel is known for its allergenic capacity and is an experimental carcinogen and equivocal tumor former. Chromium is a suspected carcinogen and an equivocal tumor producer. Beryllium is an equivocal neoplastic producer concerned with pulmonary problems that produce tumors and is an experimental carcinogen.

In additional to undesirable health side effects, laboratory fabricated porcelain/metal bridges have structural and aesthetic deficiencies. Structurally, the metal can fracture, the porcelain can fracture, and/or the porcelain/metal fused interface can separate. All of these structural failures require removal of the bridge for repair. Aesthetically, after cementation of the bridge, changes over time in pontic color or shade versus natural teeth, or bridgework fit, require removal of the bridge. All these deficiencies of indirect, laboratory fabricated porcelain/metal bridges are difficult, if not impossible, to resolve. The chronic failure of the metal-polymer-tooth bond, and the other deficiencies noted above, have prompted research into other bridgework materials, namely those in the porcelain, ceramic, and composite groups.

These other attempts to eliminate or reduce the deficiencies noted above all rely, however, on the "indirect method," that is, fabrication of bridgework in a dental laboratory or operatory. To improve the strength of the bridgework to abutment tooth bond, methyl-acrylate polymers doped with more durable filler particles, collectively known as "composites," were introduced. Attempts have also been made to affix a natural tooth or a fabricated pontic to abutment teeth utilizing webs of materials such as metal rods, carbon fiber rods, screens, films, and foils made of various materials.

U.S. Pat. No. 5,171,147, to Burgess, discloses a dental bridge prepared using the indirect method in which the bridgework pontic and attachment wings are fabricated as an integral unit out of heat-polymerized composite. Unlike traditional bridgework, the Burgess bridge does not use a metal framework, metal pontics, or fused porcelain, but like traditional bridgework, it uses the indirect method, including a pressurized oven. For installation in a patient's dental arch, the Burgess bridge requires reduction of the abutment teeth, reduction of the attachment wings to conform them with the attachment surfaces on the abutment teeth, and the use of cements or other bonding agent to fix the Burgess bridge in place. Structurally, the Burgess bridge "product" comprises not only a single, composite pontic with composite attachment wings, but the cement or other bonding agent necessary to give the bridge utility in situ.

Installing a fixed bridge without cement is contrary to the teaching of the prior art, even that of Burgess. Burgess does not disclose or claim a bridge that is bonded without a cement, or a bridge of more than one pontic, and the shown structure of the Burgess bridge has attachment contours that are useless without reduction of the abutment teeth and/or attachment wings and cementation. The Burgess bridge "product" is a two-element combination: pontic plus cement. Every claim in the Burgess patent recites, directly or indirectly, the limitation of cementing the bridge to the abutment teeth. An inventive step would be a composite bridge of one or more pontics that does not use cement or a luting agent, but is an integral bridge in situ, not a combination of "pontic plus cement." Moreover, the Burgess bridge has an implied limitation in the same way that a threaded bolt has an implied limitation. A threaded bolt requires a threaded nut or other threaded channel for utility. The Burgess bridge requires reduction of the abutment teeth for utility. All embodiments of the Burgess bridge are disclosed as requiring a reduction of the abutment teeth in the same way that a threaded bolt requires a threaded channel for utility. Fixed bridgework that in all, or virtually all, cases does not require reducing the abutment teeth is contrary to the teaching of the prior art.

Burgess describes and claims an "indirect" product that uses a bonding or luting agent different, or differently polymerized, from the pontic compound, which introduces two chemical interfaces, composite to cement, and cement to tooth. An inventive step would be bridge created in situ that does not use a different bonding or luting agent and has only one chemical interface, composite to tooth. A single compound, single chemical interface, completed product is a structurally different product from a two compound, two chemical interface, completed product. The Burgess bridge lacks utility without cement.

To use a different structural analysis, the Burgess bridge is made in a generic form that requires further adaptation for end use; it is a "workpiece" or "blank" lacking conforming attachment surfaces. The structure and form of the Burgess bridge permit it to be mass produced. In its end-product form, the Burgess bridge fits nobody without structural modifications to the cured composite and to the abutment teeth.

The indirect method has proven to be lengthy and complicated. Approximately ten laboratory steps are needed in the simplest traditional bridge construction, and with these steps come costs. Some methods are even more complex; for instance, U.S. Pat. No. 5,000,687 to Yarovesky et al. discloses an indirect method involving about 14 or 15 separate process steps. Furthermore, many indirect methods require the abutment teeth to be surgically reduced in some form; for example, the process disclosed in the patent to Yarovesky et alii requires cutting and contouring of the lingual surfaces of the abutment teeth prior to bridge installation. U.S. Pat. No. 5,120,224 to Golub, seeking to eliminate or minimize the need for abutment tooth reduction, discloses a bridge structure wherein a thin fabric laminate may be internally sandwiched within the pontic/bridge. The fabric extends outwardly from the pontic/bridge for placement on abutment teeth and for bonding thereto by an cement or luting agent.

As stated in the Golub patent, however, the disclosed structure is intended to function only as a temporary or provisional bridge. Moreover, it has been found that the placement of an inappropriate fabric or screen within composite material, particularly within the attachment wings, may weaken, rather than strengthen, the bridge framework. All laboratory-based indirect methods are therefore relatively costly, time consuming, and ineffective.

U.S. Pat. No. 4,172,323 to Orlowski discloses a method for securing a previously-made pontic or a fixed bridge, wherein a thin film or screen is applied to the appropriate surfaces on the abutment teeth. Cement or a luting agent is applied to the screens and to the attachment wings of the pontic/bridge being installed, whereafter the pontic/bridge is held in place while the cement or luting agent cures. Orlowski, however, discloses that small undercuts are made in the enamel of the abutment teeth contact areas, so as to increase the area available for bonding and resistance to shear forces. Despite that attempt to increase contact areas, it has been found that these areas are still limited such that weakness of joints results. Consequently, the securement structure disclosed by Orlowski has been found to be temporary or at best provisional, i.e., lasting considerably less than five years.

Where tooth or dental implant extraction is required before insertion of fixed dental bridgework, regardless of whether the bridgework has been constructed directly or indirectly, the traditional approach requires two to four months healing of the extraction site (alveolar socket) prior to bridge installation. The fabrication and installation of a fixed dental bridge during the same office visit as extraction of teeth or implants from the area to be bridged has heretofore been regarded as impossible.

Accordingly, there is a need in the art for a method of directly producing a permanent dental bridge that (i) eliminates invasive tooth preparation steps, (ii) can be done during the same office visit as tooth or dental implant extraction, (iii) can bridge an edentulous area of one or more alveoli, and (iv) eliminates the need for separate cementation of the bridge to the abutment teeth.

BRIEF SUMMARY OF THE INVENTION

It is thus an object of the present invention to provide a method of constructing a dental bridge which overcomes the drawbacks associated with prior art methods.

It is a further object of the present invention to provide a direct method of constructing a permanent dental bridge which is efficient, effective, and less inexpensive than traditional bridgework.

It is a further and more particular object of the present invention to provide a direct method of constructing a permanent dental bridge that contains one or more pontics and can be accomplished in situ, that is, entirely within the patient's mouth, or alternatively ex situ, at least partially constructed outside the patient's mouth.

It is a further object of the present invention to provide reinforcement of composite bridgework, especially for multi-pontic composite bridges.

These and other objects are accomplished by a method of constructing a dental bridge in situ, the dental bridge when completed occupying an edentulous space between a first abutment tooth and a second abutment tooth in a patient's mouth, comprising the steps of applying gingival laminations of a composite material, called "base composite," between the first and second abutment teeth, forming first and second attachment portions from the composite material, the attachment portions respectively attaching to corresponding surfaces on the first and second abutment teeth without the use of cement or other bonding agent, curing the composite material, and optionally introducing one or more reinforcement materials in laminations between the abutment teeth for reinforcement, whereby the dental bridge is constructed entirely within the mouth of the patient in a single office visit. After curing the laminations of base composite, additional composite material is applied between the abutment teeth, from which the first and second attachment portions and, in the in situ process, the body of one or more pontics, continue to be formed, and the additional composite material is cured. These latter steps are successively repeated, thus forming built-up laminations of composite material and optionally of reinforcement material, until the dental bridge, including at least one pontic portion, is formed and simultaneously secured to the abutment teeth.

The foregoing objects are also accomplished by a method of constructing a dental bridge ex situ, the dental bridge when completed occupying an edentulous space between a first abutment tooth and a second abutment tooth in a mouth of a patient, comprising the steps of fabricating a composite pontic ex situ, applying base composite material between attachment surfaces on the abutment teeth, curing the composite material, applying one or more laminations of additional composite material between the abutment teeth, optionally introducing one or more reinforcement materials in laminations between the abutment teeth for reinforcement, inserting the previously prepared composite pontic into the laminations of base composite and any reinforcement composite, and curing the laminations.

In the in situ process and the ex situ process, the optional reinforcing material is selected from the group comprising bondable reinforcement ribbon, metallic or non-metallic rods, metallic or non-metallic posts (including posts made of bondable reinforcement ribbon), composite material that differs from the base composite, foils, films, trusses (including tensegrity masts), and screens.

A composite with a modulus of elasticity comparatively lower than that of the base or of the reinforcement composite, can be used in the incisal, buccal, labial, and occlusal portions of a pontic, and introduces resilience and dispersion of biting and/or chewing over the base composite and any reinforcement material.

In either the in situ process or the ex situ process, a gingival stent can be utilized to act as a platform upon which the successive laminations of one or more types of composite may be formed and also, if employed immediately following tooth or implant extraction, to act as a bandage or obturator. The stent is inserted into the patient's mouth before application of composite material between the abutment teeth, and is removed after formation of the completed bridge but prior to the contouring and finishing thereof. The gingival stent comprises a base and a leaf extending from the base. The base of the stent has a lateral margin into which concave sections are formed that fit snugly around lingual surfaces of the abutment teeth and teeth adjacent thereto. When the stent is placed within the mouth, the leaf of the stent covers the gingival surface of the edentulous space to be bridged.

The fully composite bridge may contain a plurality of pontics. The greater the number of pontics included in the bridge, the more desirable it may be to introduce reinforcement material.

In summary, the foregoing objects are achieved by applying base composite between the first and second abutment teeth, forming first and second attachment portions from the base composite, the attachment portions respectively attaching to corresponding surfaces on the first and second abutment teeth, and curing the composite material to produce fixed dental bridgework. The foregoing objects are also achieved by fabricating a composite pontic ex situ, applying composite material between the first and second abutment teeth, curing the composite material, applying one or more laminations of additional composite material between the first and second abutment teeth, inserting one or more fabricated composite pontics into the one or more laminations, and curing the one or more laminations to produce fixed dental bridgework. For added strength, reinforcement material can be introduced during construction of the laminated, composite bridge. For better dispersion of biting and chewing forces, a more resilient composite can be used to form the incisal and occlusal portions of a pontic.

BRIEF DESCRIPTION OF THE SEVERAL VIEWS OF THE DRAWINGS

FIG. 1 is a palatal view of a dental arch of a mouth of a patient, showing an edentulous space of one alveolus between first and second abutment teeth.

FIG. 2 is a palatal view of a dental arch of a mouth of a patient, showing a direct, composite bridge in a one-alveolus edentulous space between first and second abutment teeth and constructed without the use of a gingival stent.

FIG. 3 is a front view of a dental arch similar to that shown in FIG. 2, showing a completed direct, composite bridge constructed of a single type of composite.

FIG. 4 is a front view of a dental arch of a mouth of a patient, showing a direct, composite bridge constructed of base composite and reinforcement material and constructed without the use of a gingival stent in a one-alveolus edentulous space between first and second abutment teeth.

FIG. 4A shows a cross-section view of the composite bridge along the a–a' datum line of FIG. 4. The core of the pontic shown in FIG. 4A contains either reinforcement material.

FIG. 4B shows a cross-section view of one attachment portion of the composite bridge along the b–b' datum line of FIG. 4. The attachment portion shown in the cross-sectional view contains only base composite.

FIG. 16 is a front view of a dental arch of a mouth of a patient, showing an edentulous space of two alveoli between first and second abutment teeth.

FIG. 17 is a front view of a dental arch of a mouth of a patient, showing a direct, composite bridge constructed in a two-alveoli edentulous space between first and second abutment teeth.

FIG. 17A is a cross-section view, along the datum line a–a' shown in FIG. 17, showing a direct, two-pontic composite bridge constructed using only base composite.

FIG. 17B is a cross-section view, along the datum line b–b' shown in FIG. 17, showing a direct, two-pontic composite bridge constructed using only base composite.

DETAILED DESCRIPTION OF THE INVENTION

Figure 5:
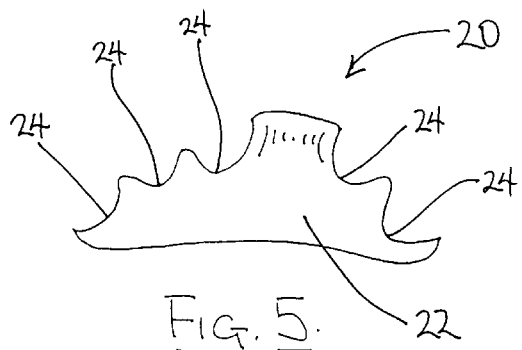
FIG. 5 is a palatal view of a gingival stent.

The "immediate, laminated, light-cured direct multi-composite bridge" comprises one or more "direct composite pontics," a bridge substructure, attachment portions, and optional reinforcement portions that are integrally fabricated and affixed in place between two or more abutment teeth in an immediate process; moreover, abutment teeth need not be reduced. "Composite" means light curable composite dental materials, such as various formulations of a colloid paste of methyl methacrylate resin and silica commonly available from dental supply houses, preferably of the type made commercially available from Prisma APH of Milford, Del. "Composite pontic" means a false tooth ("pontic") made only of light-cured composite. "Direct multi-composite pontic" means a composite pontic made without dental laboratory assistance by application and light curing of successive laminations of two or more types of composite, either in situ or ex situ, as explained below. "Direct composite bridge" means a bridge according to the present invention made using one or more types of composite. "Immediate" means that the process of fabricating and affixing the composite bridge can be completed in one office visit. The fabrication of an individual composite pontic can be performed either completely within the patient's mouth (called "in situ" or intraoral fabrication) or outside the patient's mouth (called "ex situ" or operatory fabrication). A "direct composite bridge" contrasts with traditional "indirect" methods of dental bridge construction that require fabrication of bridgework in a dental laboratory and also with methods that require the use of cement or a luting agent to affix bridgework to the abutment teeth.

Different formulations of composite have different physical characteristics; formulations that cure with higher shear and tensile strength tend to have less resilience or elasticity; formulations that cure with lower shear and tensile strength tend to have higher resilience or elasticity. A direct composite bridge may contain reinforcing material, as described below, yet also use a more resilient composite for incisal and occlusal portions of a pontic. "Base composite" means light curable composite dental materials with a modulus of elasticity acceptable for use throughout all portions of a direct composite bridge. "Reinforcement composite" means light curable composite dental materials with a modulus of elasticity comparatively higher than that of the base composite. "Finishing composite" means light curable composite dental materials with a modulus of elasticity comparatively lower than that of the base composite or of the reinforcement composite.

The in situ fabrication of an immediate laminated, light-cured composite bridge will be described in detail first, followed by detailed descriptions of the use of a gingival stent, reinforcement methods, and ex situ fabrication of such a bridge.

FIG. 1 shows a palatal view of an upper dental arch 10 of a patient's mouth. Dental arch 10 includes a row of teeth, one of which teeth has been removed, thereby leaving an edentulous (toothless) space 12 between abutment teeth, namely, a first abutment tooth 14 and a second abutment tooth 16. In the first step of the in situ method of direct composite bridge fabrication according to the present invention, each attachment surface of each abutment tooth 14, 16 is etched, preferably with a 35% phosphoric acid gel for about twenty seconds. As used herein, the term "attachment surface" means the surface areas of the abutment teeth 14, 16 to which dental composite will be applied during construction of a direct composite bridge, which attachment surfaces normally include proximal surfaces 14a, 16a (FIG. 1) and lingual surfaces 14b, 16b (FIG. 1), and may include facial surfaces 14c, 16c (FIG. 1) of abutment teeth 14 & 16.

FIG. 2 shows a palatal view of upper dental arch 10 after base composite 28 has been applied between the attachment surfaces of the abutment teeth 14, 16. Preferably, the base composite 28 is applied in a series of strings or laminations leading from the attachment surface of the first abutment tooth 14 across the edentulous space 12 to the attachment surface of the second abutment tooth 16, each string being no thicker than 1–2 mm to ensure proper photo-curing. The initial laminations of base composite are applied close to the alveolar ridge in edentulous space 12 of dental arch 10. Subsequent laminations build up the bulk of the applied base composite to create a pontic or pontic substructure, as explained below, in the region of the edentulous area 12 and to create the attachment portions 28a, 28b.

FIG. 3 shows a frontal view of dental arch 10 after base composite material 28 has been applied between the attachment surfaces of the abutment teeth 14, 16. Referring to FIGS. 2 and 3, the initial laminations of base composite 28 are smoothed with various instruments and shaped so as to begin to form a first attachment portion 28a on the attachment surface of first abutment tooth 14, and a second attachment portion 28b on the attachment surface of the second abutment tooth 16. It has been found that the attachment surface on each abutment tooth can exceed 1 cm$^2$, thus providing an exceptionally strong bridge attachment. The initial, shaped laminations of base composite 28 closest to the gingiva are then cured, preferably with a light source (not shown). Following that curing step, additional base composite is applied between the abutment teeth 14, 16, and the first and second attachment portions 28a, 28b. These steps of applying additional composite material, shaping the uncured composite material to form first and second attachment portions and a pontic in situ (or pontic substructure in the case of the ex situ process) between the abutment teeth, and curing the additional composite material are successively repeated. Each lamination should be no thicker than 1–2 mm to ensure proper photo-curing.

To ensure a broad, perfectly conforming bond by the composite material with the etched enamel in the attachment surfaces, it is important to apply continuous strings of composite material across the attachment surface, rather than merely "tacking" the end of a lamination to a single point on the attachment surface, or building and curing an attachment portion and then building and curing an adjacent pontic or pontic substructure. Preferably, the inner portion of a pontic and the external faces of an in situ pontic are concurrently built and cured as integral layers, beginning with the layer adjacent to the gingiva and ending with the crown of the pontic, rather than building and curing the substructure, then applying, shaping, and curing a veneer of composite for the external faces of the bridge. The attachment portion may include the buccal or labial portions of an abutment tooth, especially if such abutment tooth is lingually disposed. The series of shaped and cured laminations form the attachment portions and the pontic. A completed in situ, composite bridge made of a single composite material, is shown in FIG. 3.

FIG. 4 shows a frontal view of a composite bridge spanning a single alveolus edentulous area and provides datum lines a–a' and b–b' for the cross-section views in FIG. 4A and FIG. 4B, respectively. To strengthen a composite bridge, reinforcement materials can be introduced in the core area 100 (FIG. 4A) of the bridge during construction of the bridge. To construct a reinforced composite bridge, after applying, shaping, and curing laminations of base composite in the layer adjacent to the gingiva, reinforcing material selected from the group consisting of reinforcement composite, bondable reinforcement ribbon, metallic or non-metallic rods, foils, films, trusses, masts, and screens is inserted or applied in or near core area 100 of the bridge. Reinforcement composite can be applied so that it does, or does not, form part of the attachment portions 28a, 28b. FIG. 4B shows a cross-section of a reinforced composite bridge in which only base composite comprises the attachment portion. Various types of reinforced composite bridges are described in detail, and common sources of reinforcement materials are identified, after the following sections about the use of a gingival stent and of construction of multi-pontic composite bridges.

Figure 6:
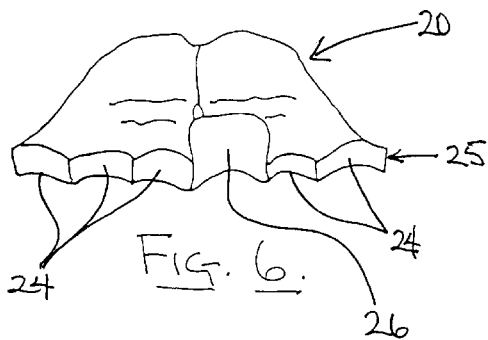
FIG. 6 is a front view of the gingival stent shown in FIG. 5.
Figure 7:
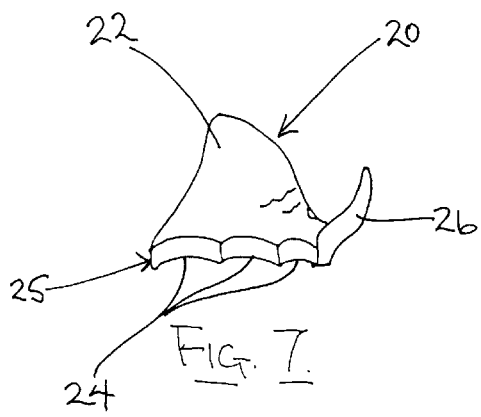
FIG. 7 is a side view of the gingival stent shown in FIG. 5.

If the missing tooth or dental implant has been extracted immediately prior to the time of bridge fabrication and installation, then it has been found that the use of a gingival stent is particularly advantageous. Referring to FIGS. 5, 6, and 7, to control, form, and contour the flow of uncured composite laminations over the edentulous space 12 (FIGS. 1 & 2) prior to solidification by light curing, a gingival stent 20 is used. The gingival stent 20 is installed commencing approximately five minutes after tooth or dental implant extraction is completed. The gingival stent 20 has a dual function: it acts as a bandage or obturator stabilizing the clotting process in the alveolar socket (if tooth extraction occurs during the same office visit as bridge formation), and it also serves as a platform upon which the composite bridge is fabricated.

Referring to FIGS. 5, 6, & 7, the gingival stent 20 includes a base 22 having a lateral margin 25 (FIGS. 6 and 7) into which a plurality of concave sections 24 are formed. Concave sections 24 are dimensioned to snugly fit around lingual surfaces of the abutment teeth 14, 16 and teeth adjacent thereto (such as teeth 15, 17, 19 in FIG. 1). A leaf 26 (FIGS. 6 & 7) extends from the facial margin 25 of the base 22; the leaf's shape conforms to the gingival surface in the edentulous space 12 (FIG. 1) when the gingival stent 20 is placed within the patient's mouth. Preferably, leaf 26 is formed integrally with the base 22 such that the leaf 26 and the base 22 form a one-piece structure.

The gingival stent 20 is preferably constructed with vinyl polysiloxane impression material or equivalent, such as that commercially available as type "o" putty from GC America, Inc. of Chicago, Ill. under the trademark EXAFLEX. The material is mixed in hand and adapted to the lingual surfaces of the abutment teeth and adjacent teeth, molded intraorally and interdentally where possible, to cover the entire edentulous ridge to the facial cervical, defined as the substantially straight datum line a–a' in FIG. 9, passing through or very near the cervical surface (the area where the gum meets the tooth) of each of the abutment teeth 14, 16. The lateral face 25 of gingival stent 20 should be even, in a horizontal attitude, with the tooth cervical areas. The setting agent in the polysiloxane material causes the gingival stent 20 to solidify as formed. When set, the gingival stent 20 is removed and contoured with a fine fluted finishing bur to minimal acceptable thickness. During the months that follow the extraction, the alveolar ridge in the edentulous area 12 gradually shrinks as it heals; this shrinkage exposes a space gingival to the tissue side of the composite bridge. That space is easily closed by applying additional composite in the gingival space and light curing the composite to the existent bridge. Some space should be left for hygienic irrigation, however.

Figure 9:
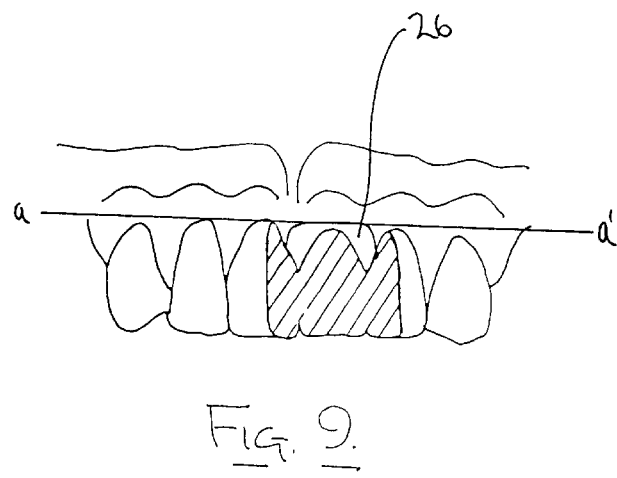
FIG. 9 is a front view of the dental arch shown in FIG. 8, showing a direct, single composite bridge, constructed with the use of a gingival stent, and shown before removal of the gingival stent.
Figure 8:
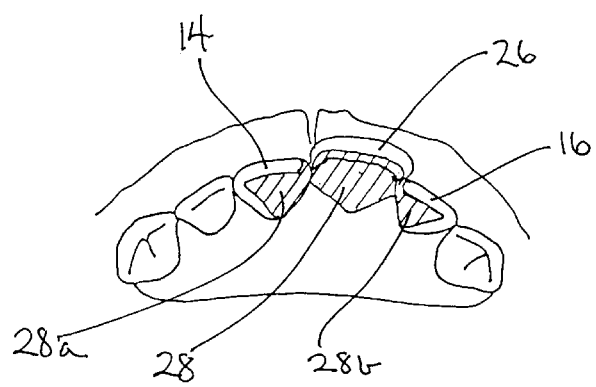
FIG. 8 is a palatal view of a dental arch of a mouth of a patient, showing a direct, composite bridge constructed of a single type of composite in a one-alveolus edentulous space between first and second abutment teeth and constructed with the use of a gingival stent, and shown before removal of the gingival stent.

Referring to FIGS. 8 & 9, the gingival stent 20 is inserted into the patient's mouth before application of any composite material. FIGS. 8 & 9 show a direct composite bridge constructed using a single composite material, and additionally shows the leaf 26 of the gingival stent 20 covering the previously-exposed alveolar ridge in the edentulous area 12; the lateral faces of leaf 26 are contiguous with both abutment teeth 14, 16. The leaf 26 of the stent 20 acts as a platform for the placement of the base composite 28, meaning that the composite material occupying the edentulous space 12 contacts the stent face on the opposite side of leaf 26 from the gingiva during the bridge fabrication process.

Figure 10:
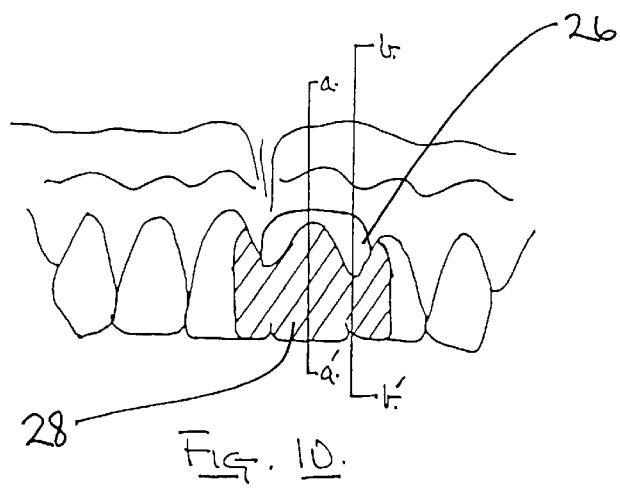
FIG. 10 is a front view of a dental arch of a mouth of a patient, showing a direct, composite bridge constructed using base composite and reinforcement material and constructed with the use of a gingival stent in a one-alveolus edentulous space between first and second abutment teeth.
Figure 11:
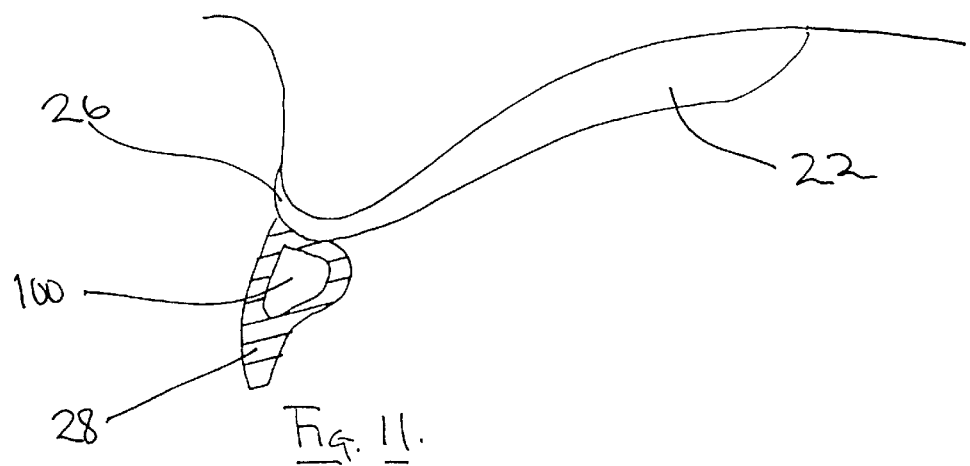
FIG. 11 is a cross-section view, along the datum line a–a' shown in FIG. 10, of a direct, composite bridge constructed using base composite, reinforcement material in the core of the pontic, and a gingival stent.
Figure 12:
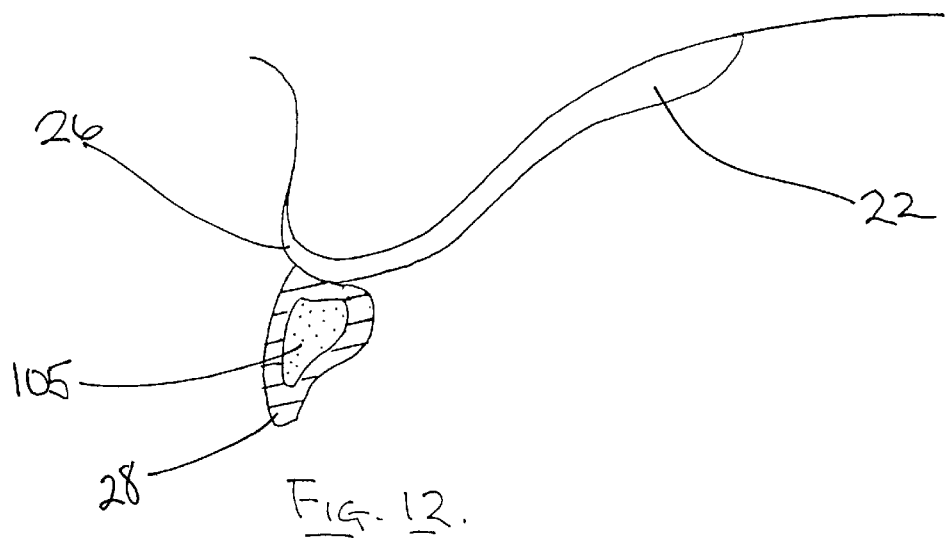
FIG. 12 is a cross-section view, along the datum line a–a' shown in FIG. 10, of a direct, composite bridge constructed using base composite, reinforcement composite in the core of the pontic, and a gingival stent.

To construct a reinforced composite bridge using a gingival stent, a gingival stent is formed and inserted intraorally in the same manner as for a stent-assisted bridge constructed of a single composite material. FIG. 10 shows a frontal view of a composite bridge spanning a single alveolus edentulous area, and provides datum lines a–a' and b–b' for the cross-section views in FIG. 11 and FIG. 12, respectively. The gingival stent is used as a platform for the initial laminations of base composite, and reinforcement materials are introduced in or near core area 100 (FIG. 11) of the bridge during construction of the bridge. Other than the insertion and removal of the stent, the process of constructing a reinforced composite bridge is the same as described above for constructing a reinforced composite bridge without using a gingival stent. FIG. 12 is a cross-section view, along the datum line a–a' shown in FIG. 10, of a direct, composite bridge constructed using base composite, reinforcement composite 105 in core area 100, and a gingival stent. The gingival stent is removed no later than the completion of the direct composite bridge.

Figure 13:
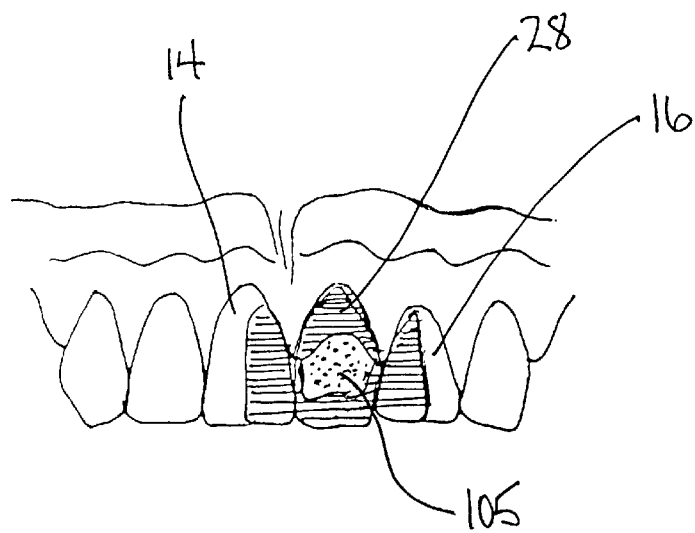
FIG. 13 is a cross-section view, along the datum line a–a' shown in FIG. 2, showing a direct, composite bridge constructed using base composite that does contact abutment teeth and reinforcement composite that does not contact the abutment teeth.
Figure 14:
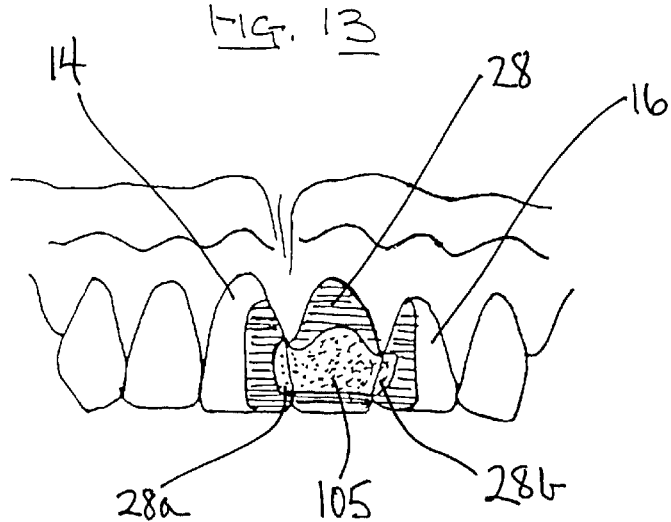
FIG. 14 is a cross-section view, along the datum line a–a' shown in FIG. 2, showing a direct, composite bridge constructed using base composite and reinforcement composite that does contact the abutment teeth.

As explained above, if a stent is not used, the laminations of base composite in the edentulous area 12 (FIG. 1) are placed atop the alveolar ridge. Use of a gingival stent may not be necessary if a patient's alveolar ridge has healed following tooth or implant extraction prior to a given office visit, which would be the case if a direct composite bridge were replacing traditional cemented bridgework. When constructing direct composite bridgework over a healed alveolar ridge in a patient's maxillary arch, gravity tends to create a gap between gingiva and composite), and when constructing direct composite bridgework over a healed alveolar ridge in a patient's maxillary or mandibular arch, residual saliva on the alveolar ridge tends to create a gap between gingiva and composite; the gingival gap thereby created, upon completion of the direct composite bridge, is acceptable for hygienic irrigation of the alveolar ridge proximal to the bridge. During application of the reinforcement composite in the core area 100 (FIG. 4A), laminations of reinforcement composite are applied that either do not terminate on the attachment surfaces, as shown in FIG. 13, or terminate on the attachment surfaces, as shown in FIG. 14. FIG. 13 shows a cross-section view, along the datum line a–a' shown in FIG. 2, of a direct, composite bridge constructed using base composite that does contact abutment teeth and reinforcement composite that does not contact the abutment teeth.

Reinforcement composite has a higher modulus of elasticity than base composite, and tends to flex less than base composite and to disperse incisal and occusal forces across the area in which reinforcement composite is applied. Whether the less flexible reinforcement composite should be part of the attachment portion, and thereby convey incisal or occlusal forces more directly to the abutment teeth 14, 16, is in part determined by how strong, and how strongly affixed in the mandible or maxilla, the abutment teeth are. FIG. 14 is a cross-section view, along the datum line a–a' shown in FIG. 2, showing a direct, composite bridge constructed using base composite and reinforcement composite that both contact the abutment teeth. The remaining steps in completing the direct composite bridge are as described above.

Figure 15:
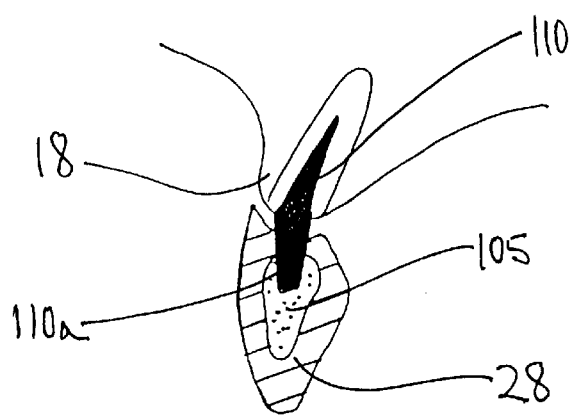
FIG. 15 is a cross-section view, along the datum line a–a' shown in FIG. 4, showing a direct, composite bridge constructed using base composite, reinforcement composite, and an endodontic post.

An endodontic post can be used to reinforce a direct composite bridge. Unlike other reinforcement materials, which are embedded in, near, or as, the core laminations of the pontic, endodontic posts protrude through the alveolar ridge 18 (FIG. 15), through the initial laminations of base composite, and into the core area of the pontic. FIG. 15 is a cross-section view, along the datum line a–a' shown in FIG. 4, showing a direct, composite bridge constructed using an endodontic post 110 anchored in the alveolar ridge 18, with the protruding portion 110a of the endodontic post embedded in base composite 28 and reinforcement composite 105. If crowns on posts are to be replaced by a direct composite bridge, the crowns are reduced to reveal the posts. The exposed posts can be shaped to provide reinforcement for a direct composite bridge or reduced to be flush with the top of the alveolar ridge. Posts protruding above the alveolar ridge normally preclude, or complicate, the use of a gingival stent. The protruding portion 110a of an endodontic post 100 is etched, preferably with a 35% phosphoric acid gel for about twenty seconds, at the same time the attachment surfaces are etched. The initial and subsequent laminations of composite are applied to encase the protruding portion 110a of the endodontic post 110. The remaining steps in completing the direct composite bridge are as described above. Reinforcement of a direct composite bridge using an endodontic post is normally not used unless the alveolar ridge around the post has healed, thereby minimizing the need for use of a gingival stent and possible problems related to seating of the post in the mandibular or maxillary arch. Care should be taken so that the protruding portion 110a of the endodontic post 110 does not terminate too close to the buccal or labial surface of the pontic and thereby discolor the pontic.

A direct composite bridge can span an edentulous area of more than one alveolus. FIG. 16 is a front view of a dental arch of a mouth of a patient, showing an edentulous space of two alveoli between first and second abutment teeth. FIG. 17 shows a direct, composite bridge constructed in a two-alveoli edentulous space 112 (FIG. 16) between first and second abutment teeth 14, 16. The steps in constructing a direct composite bridge that spans an edentulous area of more than one alveolus are as described above for a direct composite bridge that spans an edentulous area of one alveolus, except for the greater distance between abutment teeth 14, 16 across which the composite and any reinforcement materials must be applied. FIG. 17A is a cross-section view, along the datum line a–a' shown in FIG. 17, showing a direct, two-pontic composite bridge constructed using a single composite 28. The cross-section view in FIG. 17 along datum line c–c' is substantially identical to that along datum line a–a'. FIG. 17B is a cross-section view of the attachment portion along the datum line b–b' shown in FIG. 17, showing a direct, two-pontic composite bridge constructed using a single composite 28 in the attachment portion 28a.

Figure 18:
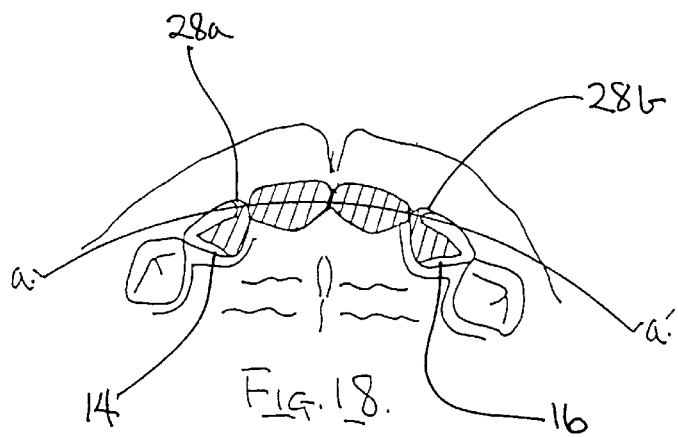
FIG. 18 is a palatal view of the dental arch substantially similar to the one shown in FIG. 17, showing a completed direct, two-pontic composite bridge.
Figure 19:
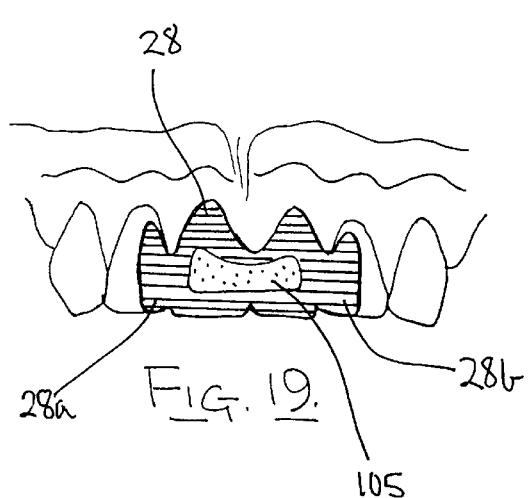
FIG. 19 is a cross-section view, along the datum line a–a' shown in FIG. 18, showing a direct, two-pontic composite bridge constructed using base composite that does contact abutment teeth and reinforcement composite that does not contact the abutment teeth.
Figure 19A:
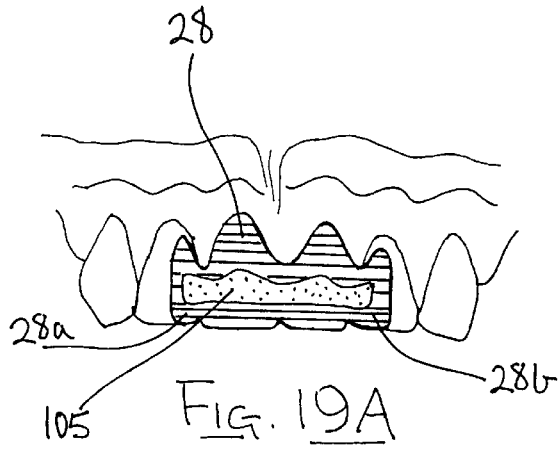
FIG. 19A is a cross-section view, along the datum line a–a' shown in FIG. 18, showing a direct, two-pontic composite bridge constructed using base composite that does contact abutment teeth and reinforcement composite that does contact the abutment teeth.
Figure 21:
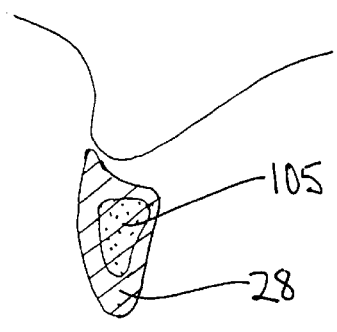
FIG. 21 is a cross-section view, along the datum line b–b' shown in FIG. 17, showing a direct, two-pontic composite bridge constructed using base composite and reinforcement composite.
Figure 20:
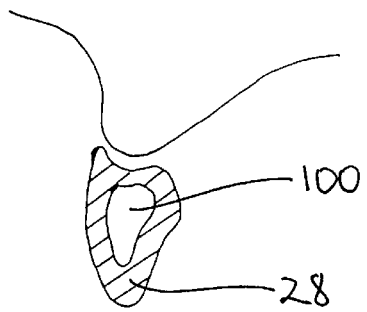
FIG. 20 is a cross-section view, along the datum line a–a' shown in FIG. 17, showing a direct, two-pontic composite bridge constructed using base composite and with a pontic core that contains reinforcement material.

Reinforcement composite can be applied entirely within the substructure of the pontics in a multi-pontic direct composite bridge, so that the reinforcement composite does not contact the abutment teeth 14, 16. FIG. 19 shows a cross-section view, along the datum line a–a' shown in FIG. 18, of a direct, two-pontic composite bridge constructed using base composite that does contact abutment teeth and reinforcement composite that does not contact the abutment teeth. FIG. 19A is a cross-section view, along the datum line a–a' shown in FIG. 18, showing a direct, two-pontic composite bridge constructed using base composite and reinforcement composite that both contact the abutment teeth 14, 16. The factors that determine whether the reinforcement composite should attach directly to the abutment teeth are the same in multi-pontic composite bridges as in single pontic reinforced composite bridges, as described above. During application of the reinforcement composite in the core area 100 (FIG. 20), laminations of reinforcement composite are applied that either terminate on the attachment surfaces, as shown in FIG. 19A, or do not terminate on the attachment surfaces, as shown in FIG. 19. The remaining steps in completing the direct composite bridge are as described above. FIG. 21 is a cross-section view of the attachment portion along the datum line b–b' shown in FIG. 17, showing a direct, two-pontic composite bridge constructed using base composite 28, and reinforcement composite 105 in the core of the pontic.

Figure 22:
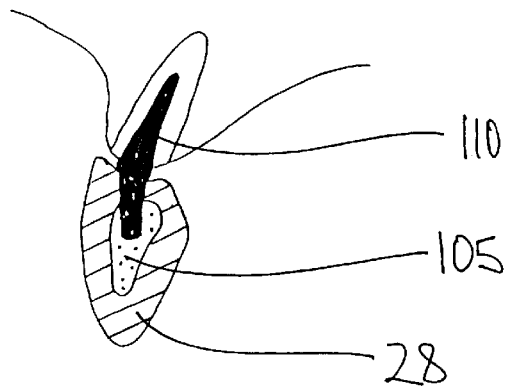
FIG. 22 is a cross-section view, along the datum line a–a' of the multi-pontic bridge shown in FIG. 17, showing a direct, composite bridge constructed using base composite, reinforcement composite, and an endodontic post. The cross-section view along the datum line c–c' shown in FIG. 17 is the same as FIG. 22.

An endodontic post can be used to reinforce a multi-pontic, direct composite bridge. The steps in constructing an endodontic post-reinforced, multi-pontic, direct composite bridge are as described above for an endodontic post-reinforced, direct composite bridge that spans an edentulous area of one alveolus, except for the greater distance between abutment teeth 14, 16 across which the composite and any longitudinal reinforcement materials must be applied, and the use of more than one endodontic post. FIG. 22 is a cross-section view, along the datum line a–a' of the two-pontic bridge shown in FIG. 17, showing a direct composite bridge constructed using base composite 28, reinforcement composite 105, and an endodontic post 110. The cross-section view, along the datum line c–c' shown in FIG. 17, is the same as that shown in FIG. 22.

In addition to the use of reinforcement composite and of endodontic posts for reinforcement, other materials can be used, e.g., bondable reinforcement ribbon, metallic or non-metallic rods, foils, films, trusses, masts, or screens. These reinforcement materials can be used in either single pontic, or multi-pontic, composite bridges. When bondable reinforcement ribbon, metallic or non-metallic rods, foils, films, trusses, or screens are used, after lamination and curing of the initial one or more layers of base composite, the selected reinforcement material is held in place in or near the core area 100 (FIG. 20) by laminations of composite material (either base composite or reinforcement composite), then additional laminations of base composite are applied between the attachment surfaces 28a, 28b (FIG. 18) and shaped to form the external faces of the attachment portions and pontic, and then all composite in the layer just applied is cured, securing the reinforcement material in place. It is important to avoid introducing air pockets or contaminants when laminating the reinforcement material in place. Additional laminations of composite are applied in and near core area 100 and other portions of the bridge (either base composite or reinforcement composite, according to the type and placement used in the just-cured laminations), shaped, and cured. The bridge is thereafter completed in the manner described for a composite bridge reinforced only with reinforcement composite in core area 100.

Figure 23:
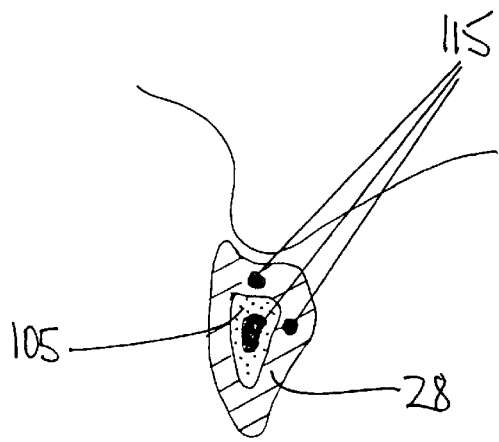
FIG. 23 is a cross-section view, along the datum line a–a' of the multi-pontic bridge shown in FIG. 17, showing a direct, composite bridge constructed using base composite, reinforcement composite, and rod reinforcement.

FIG. 23 is a cross-section view, along the datum line a–a' of the multi-pontic bridge shown in FIG. 17, showing a direct, composite bridge constructed using base composite 28, reinforcement composite 105, and rod reinforcement 115. The rod reinforcement 115 is shown embedded both in base composite 28 and in reinforcement composite 105, but could have been embedded in only one type of composite. Rod reinforcement is available from Moyco Union Broach Division, 589 Davies Drive, York, Pa. 17402.

Figure 24:
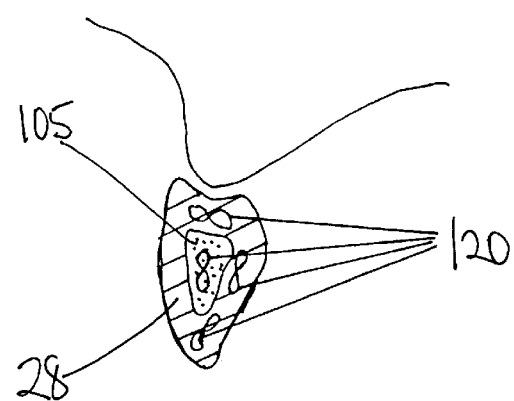
FIG. 24 is a cross-section view, along the datum line a–a' of the multi-pontic bridge shown in FIG. 17, showing a direct, composite bridge constructed using base composite, reinforcement composite, and ribbon reinforcement.

FIG. 24 is a cross-section view, along the datum line a–a' of the multi-pontic bridge shown in FIG. 17, showing a direct, composite bridge constructed using base composite 28, reinforcement composite 105, and bondable ribbon reinforcement 120. The bondable ribbon reinforcement 120 is shown embedded both in base composite 28 and in reinforcement composite 105, but could have been embedded in only one type of composite. Bondable ribbon reinforcement is specially made to form strong bonds with dental composite materials. Bondable ribbon reinforcement is available from Ribbond, Inc., 1402 Third Ave., Ste 1030, Seattle, Wash. 98101.

Figure 25:
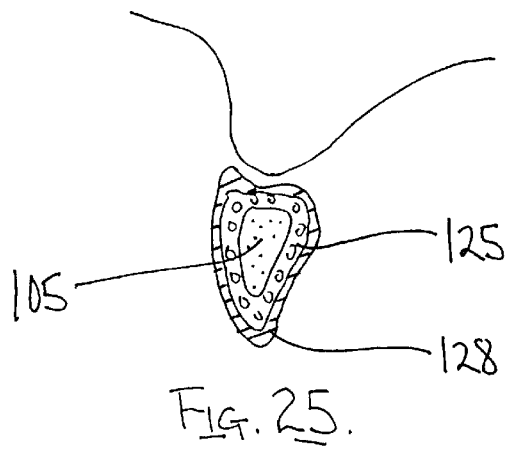
FIG. 25 is a cross-section view, along the datum line a–a' of the multi-pontic bridge shown in FIG. 17, showing a direct, composite bridge constructed using base composite, reinforcement composite, and film reinforcement.

FIG. 25 is a cross-section view, along the datum line a–a' of the multi-pontic bridge shown in FIG. 17, showing a direct, composite bridge constructed using base composite 28, reinforcement composite 105, and foil or film reinforcement 125. The foil or film reinforcement 125 is shown embedded only in base composite 28, although it could also have been embedded in reinforcement composite 105. Foil and film reinforcement is available from Glasspan, Inc., 101 John Robert Thomas Drive, Extion Pa. 19341.

Figure 26:
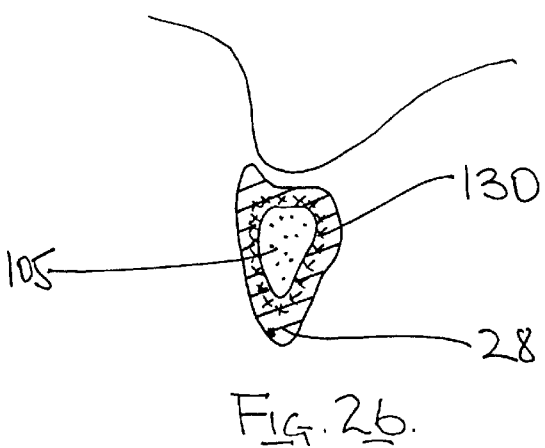
FIG. 26 is a cross-section view, along the datum line a–a' of the multi-pontic bridge shown in FIG. 17, showing a direct, composite bridge constructed using base composite, reinforcement composite, and screen reinforcement.

FIG. 26 is a cross-section view, along the datum line a–a' of the multi-pontic bridge shown in FIG. 17, showing a direct, composite bridge constructed using base composite 28, reinforcement composite 105, and screen reinforcement 130. The screen reinforcement 130 is shown embedded only in base composite 28, although it could also have been embedded in reinforcement composite 105. Screen reinforcement is available from Jordco, Inc., 595 N.W. 167th Avenue, Beaverton, Oreg. 97006.

Figure 27:
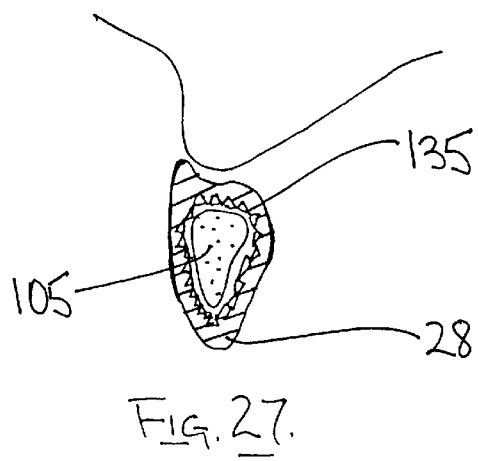
FIG. 27 is a cross-section view, along the datum line a–a' of the multi-pontic bridge shown in FIG. 17, showing a direct, composite bridge constructed using base composite, reinforcement composite, and truss reinforcement.

FIG. 27 is a cross-section view, along the datum line a–a' of the multi-pontic bridge shown in FIG. 17, showing a direct, composite bridge constructed using base composite, reinforcement composite, and truss reinforcement. The truss reinforcement 135 is shown embedded only in base composite 28, although it could also have been embedded in reinforcement composite 105. Truss reinforcement is available from Gramm Technology, Inc., 3016 PS Business Center, Woodbridge, Va. 22192.

Figure 28:
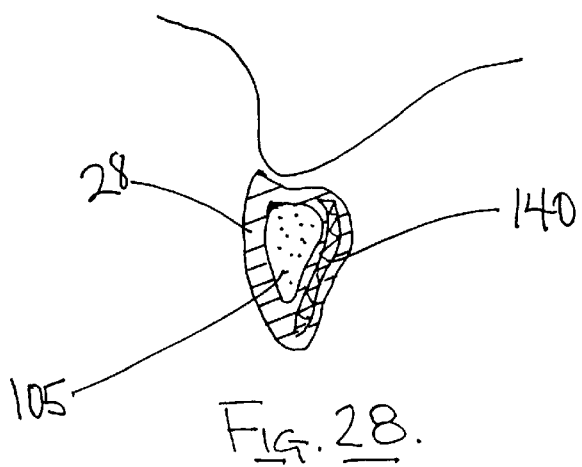
FIG. 28 is a cross-section view, along the datum line a–a' of the multi-pontic bridge shown in FIG. 17, showing a direct, composite bridge constructed using base composite, reinforcement composite, and tensegrity mast reinforcement.

FIG. 28 is a cross-section view, along the datum line a–a' of the multi-pontic bridge shown in FIG. 17, showing a direct, composite bridge constructed using base composite, reinforcement composite, and tensegrity mast reinforcement. The tensegrity mast reinforcement 140 is shown embedded only in base composite 28, although it could also have been embedded in reinforcement composite 105. Tensegrity mast reinforcement is custom made according to the description of tensegrity technology in "Cosmography," by R. Buckminster Fuller, Macmillian Publishing Co.

Figure 29:
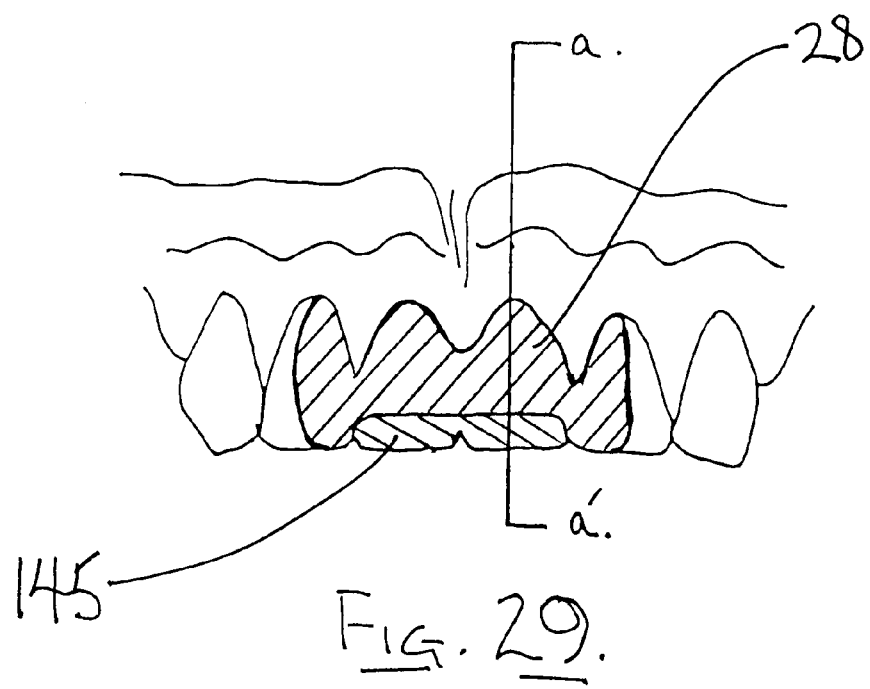
FIG. 29 is a front view of a dental arch of a mouth of a patient, showing a direct, two-pontic composite bridge constructed of base composite and of finishing composite on incisal and facial portions of the pontics in a two-alveoli edentulous space between first and second abutment teeth.
Figure 30:
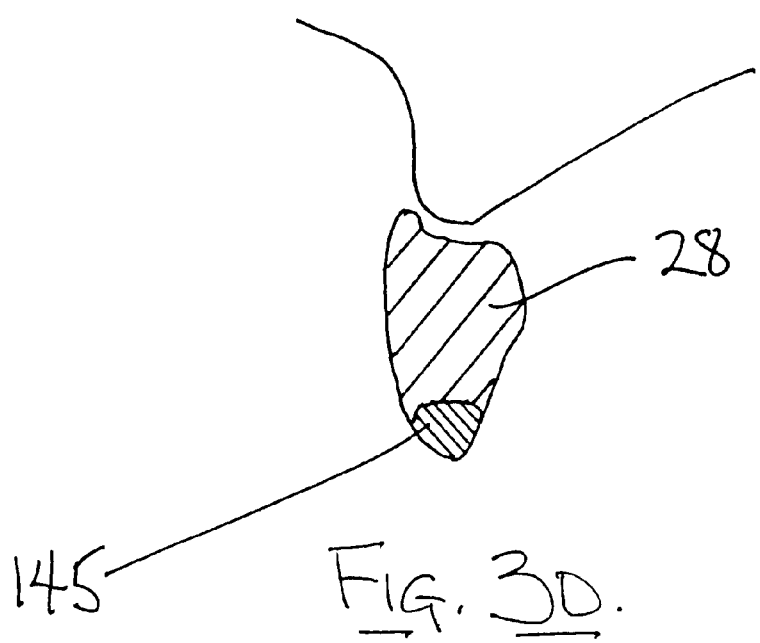
FIG. 30 is a cross-section view, along the datum line a–a' shown in FIG. 29, showing a direct, two-pontic composite bridge constructed using base composite and finishing composite on incisal and facial portions of the pontics.

A composite with a comparatively lower modulus of elasticity than the reinforcement composite, when used in the incisal and occlusal portions of a pontic, introduces resilience and dispersion of biting and/or chewing over the base composite and over any reinforcement material. A composite that responds better to polishing, or is more stain resistant, than base composite may be selected for the incisal, occlusal, labial, and/or buccal portions of composite pontics. The composite used for the incisal, occlusal, labial, or buccal portions of a pontic, if different from the base composite and reinforcement composite, is called "finishing composite". Finishing composite can be used in single-pontic composite bridges or in multi-pontic composite bridges. FIG. 29 is a front view of a direct, two-pontic composite bridge constructed of primarily of base composite 28, but with finishing composite 145 in the incisal and some facial portions of the pontics. The steps in constructing a direct composite bridge that includes finishing composite are as described above for any of the other reinforced or unreinforced, direct composite bridges, except that the final laminations of composite in the incisal, occlusal, labial, and/or buccal portions of the pontics are made using finishing composite. After shaping and curing of the finishing composite, the bridge is contoured and finished. FIG. 30 is a cross-section view, along the datum line a–a' shown in FIG. 29, showing a direct, two-pontic composite bridge constructed using base composite 28 for all but the laminations in the incisal and some facial portions of the pontic, and finishing composite 145 in the incisal and some facial portions of the pontics.

Figure 31:
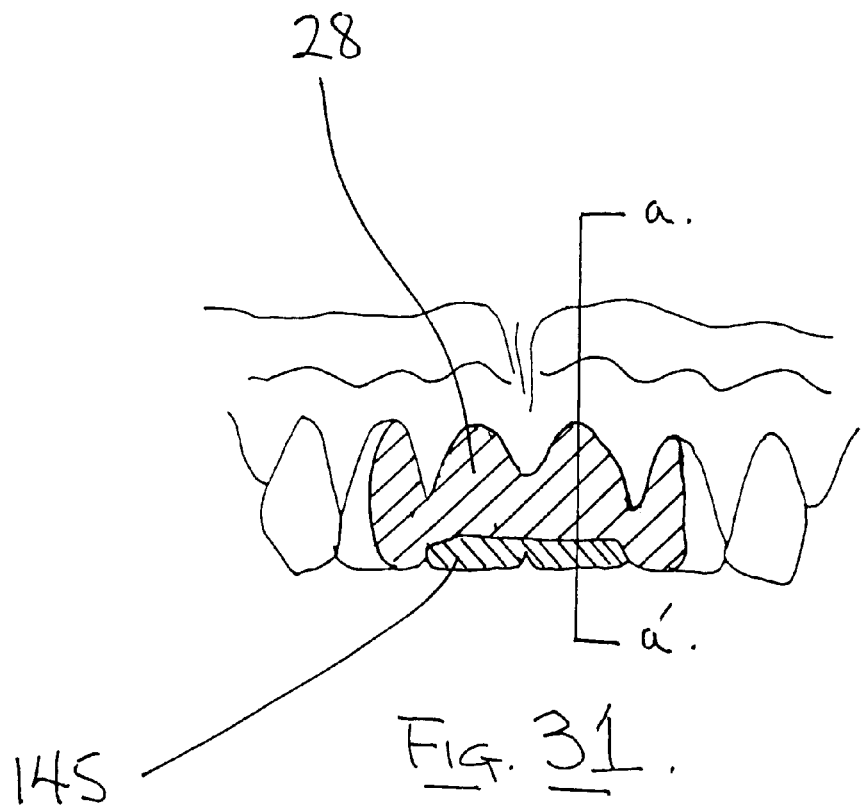
FIG. 31 is a front view of a dental arch of a mouth of a patient, showing a direct, two-pontic composite bridge constructed of base composite, reinforcement material, and finishing composite in a two-alveoli edentulous space between first and second abutment teeth.
Figure 32:
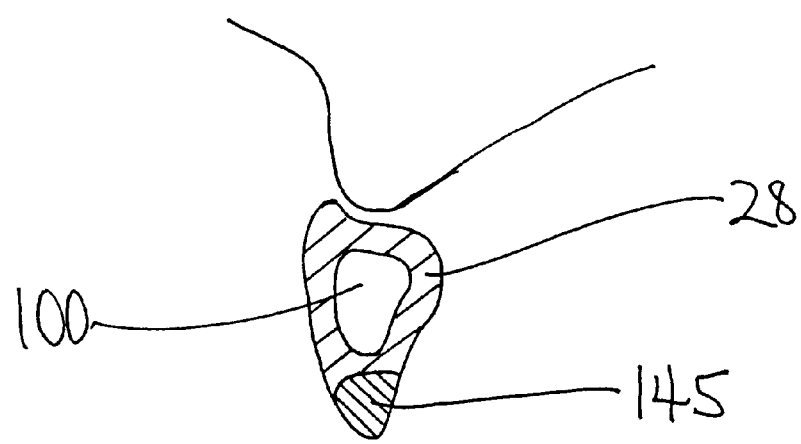
FIG. 32 is a cross-section view, along the datum line a–a' shown in FIG. 31, showing a direct, two-pontic composite bridge constructed using base composite, reinforcement material in the core area of the pontic, and finishing composite.
Figure 33:
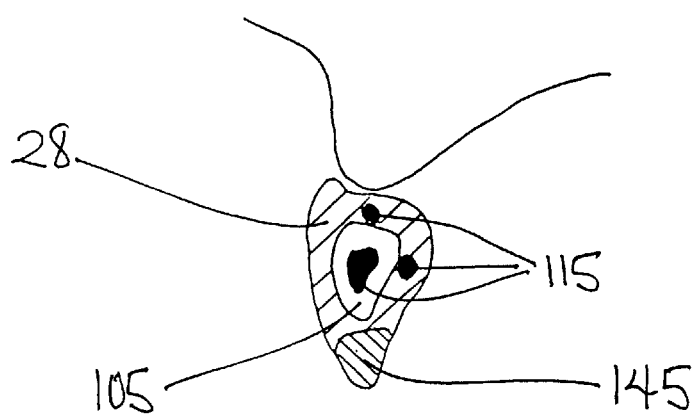
FIG. 33 is a cross-section view, along the datum line a–a' shown in FIG. 31, showing a direct, two-pontic composite bridge constructed using base composite, reinforcement composite, rod reinforcement, and finishing composite.

As alluded to above, finishing composite can also be used in reinforced, direct composite bridges, both single pontic and multi-pontic. FIG. 31 shows a direct, two-pontic composite bridge constructed of base composite, reinforcement material, and finishing composite. FIG. 32 is a cross-section, along the datum line a–a' shown in FIG. 31, showing a direct, two-pontic composite bridge constructed using base composite 28, core area 100 (containing base composite or reinforcement material) of the pontic, and finishing composite 145. Reinforcement of a direct, composite bridge that includes finishing composite is not limited to the use of reinforcement composite, and can include any of the reinforcement methods described above. FIG. 33 is a cross-section view, along the datum line a–a' shown in FIG. 31, showing a direct, two-pontic composite bridge constructed using base composite 28, reinforcement composite 105, rod reinforcement 115, and finishing composite 145. The steps in constructing a reinforced, direct composite bridge that includes finishing composite are as described above for any of the other reinforced direct composite bridges, except that the final laminations of composite in the incisal, occlusal, labial, and/or buccal portions of the pontics are made using finishing composite.

Shaping of composite is done before curing of the fresh laminations of composite. Viscosity of most types of light-cured composite is proportional to the proximity and length of irradiation by a curing light. The iterations of lamination, irradiation, and shaping are a matter of composite formulation, pontic or attachment portion being built, and individual preference and skill. The final laminations of composite may include extra laminations of composite, called "overbulked composite", to insure adequate pontic volume, especially when final shaping is to be done by reduction of cured composite. It is critical when applying composite to avoid the introduction of air bubbles and contaminants.

The application, shaping, and curing of laminations ceases when a composite dental bridge, including the attachment portions and all portions of each pontic, has been formed. The bridge resulting from this novel process of fabrication is a solid, acceptably flexible, high strength structure that integrates pontics, attachment portions, substructure, and optional reinforcement. Once a direct, composite bridge has been formed, any gingival stent 20 (FIG. 5), including its leaf 26, that was used during bridge construction is removed from the patient's mouth and discarded. Stent removal is made possible by the fact that the gingival stent 20, being constructed of material differing from the composite material comprising the bridge, does not chemically fuse or weld to the composite. Without such adhesion, the gingival stent 20, once the composite has been cured, easily slides from beneath the bridge pontic portion and from around the abutment teeth 14, 16 and teeth adjacent thereto.

As a final step in the in situ process, the bridge is contoured and finished, i.e., any "overbulked" composite is trimmed with various rotary instruments such as diamond burs, fine fluted finishing burs, and rubber wheels, then finished with polishing paste. If an error is made during finishing, the area of the error can be cleaned of debris, appropriate composite (base or finishing) applied, shaped, and cured, and then finished.

In the ex situ process, which will now be described in detail, a composite pontic must first be fabricated outside the patient's mouth, e.g., in an operatory.

Figure 34:
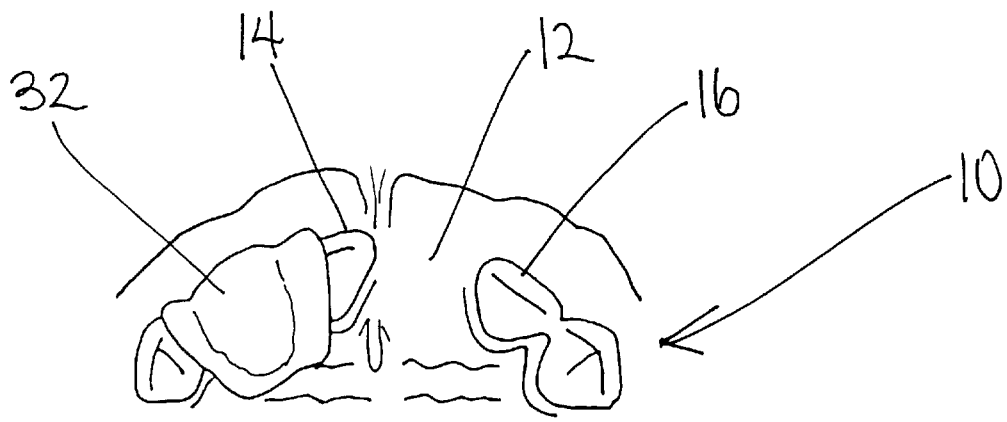
FIG. 34 is a palatal view of a dental arch with a layer of wax pressed upon a lateral incisor within the arch.
Figure 35:
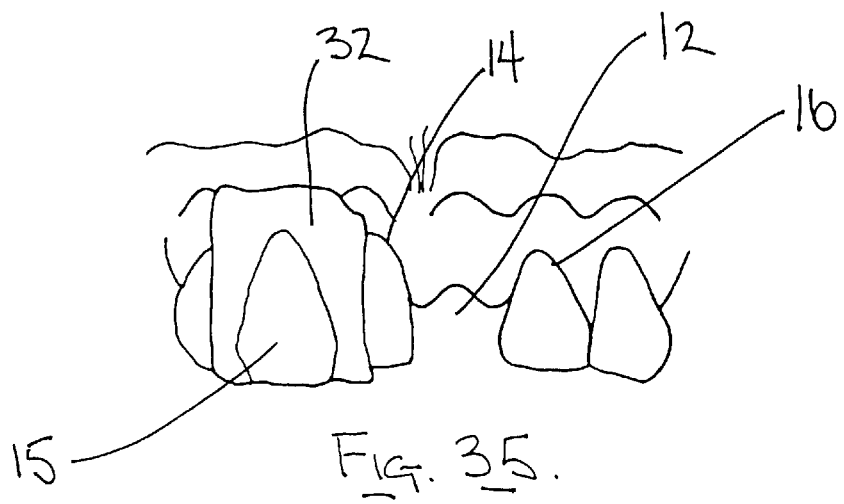
FIG. 35 is a front view of a dental arch with a layer of wax pressed upon a lateral incisor within the arch.

In FIGS. 34 & 35, a layer of warm wax is placed over another tooth, such as lateral incisor 15, within dental arch 10, thereby forming a wax mold 32 of lateral incisor 15. The wax used to comprise mold 32 is preferably a number 3 wax, commercially available from Miles, Inc. of South Bend, Indiana under the trademark MODERN MATERIALS.

Figure 36:
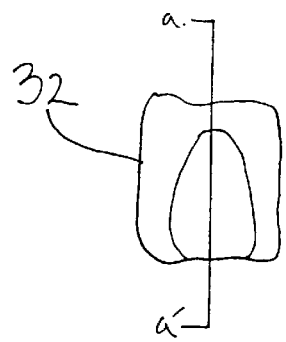
FIG. 36 is a front view of a cooled, empty wax mold formed from the layer of wax illustrated in FIG. 35.
Figure 37:
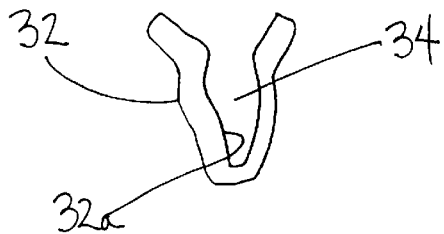
FIG. 37 is a cross-section view of the mold, taken along datum line a–a' in FIG. 36.
Figure 38:
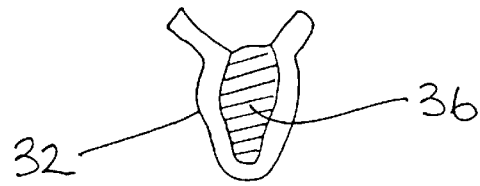
FIG. 38 is a cross-section view of the mold, taken along datum line a–a' in FIG. 36, showing a composite filled within the mold.

Referring to FIGS. 36, 37, & 38, the mold 32 is removed from the lateral incisor 15 (FIG. 1) and is allowed to cool. As seen in FIG. 37, the mold 32 has a somewhat V-shaped profile, whereby an internal wall 32a of the mold 32 defines an internal chamber 34. A layer of un-filled resin polymer is placed within mold 32 and is then cured. The layer of unfilled resin polymer acts as a lubricant on wall 32a and allows for ease of removal of the completed pontic from the mold 32, to be described later herein. Next, layers of a filled resin polymer are successively placed within the mold 32, preferably at a thickness each of 1 mm to 2 mm, and cured until a completed composite pontic 36 is formed within the mold 32, as shown in FIG. 38.

Figure 39:
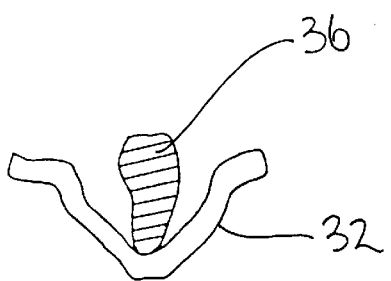
FIG. 39 is a side elevation view of the wax mold, substantially similar to mold in FIG. 38, being opened and separated from cured composite, which now forms a pontic.
Figure 40:
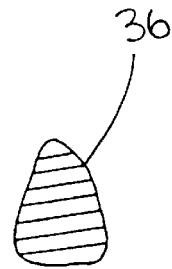
FIG. 40 is a front view of the pontic shown in FIG. 39.
Figure 41:
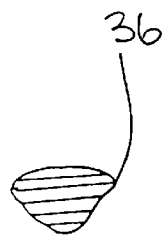
FIG. 41 is a plan view of the pontic shown in FIG. 39.

As depicted in FIGS. 39, 40, & 41, the mold 32 is peeled back, or removed, from the completed pontic 36, which is seen as being substantially identical to the lateral incisor 15 from which the mold 32 was formed. Although these figures show a single pontic 36, the term "pontic", as used in the claims stated herein, shall be construed to mean a plurality of pontics (if the patient is initially missing more than one tooth), as well as a singular pontic.

Figure 42:
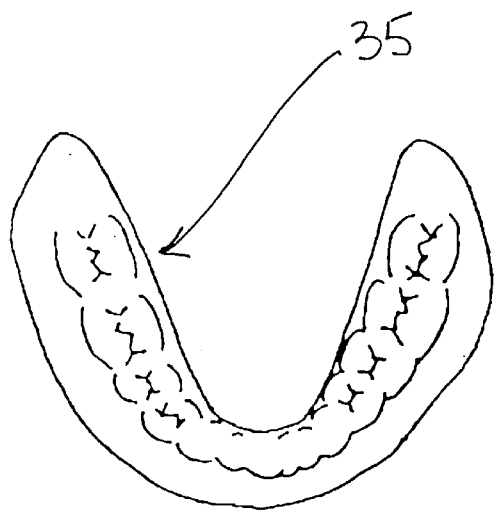
FIG. 42 is a plan view of a crown form which is used to fabricate a pontic in accordance with a modified ex situ process of the present invention.
Figure 43:
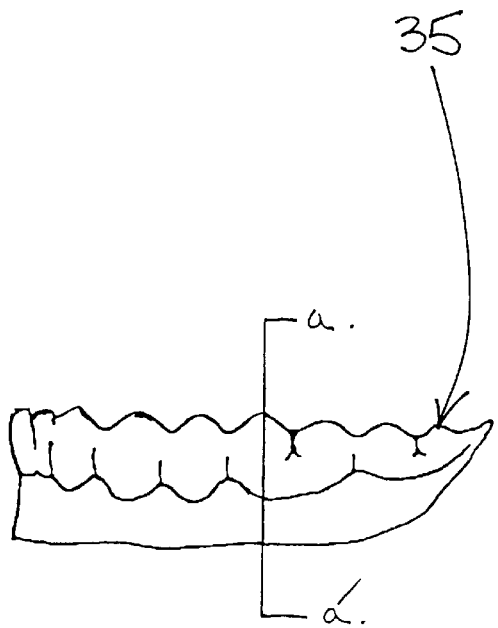
FIG. 43 is a side view of the crown form shown in FIG. 42.
Figure 44:
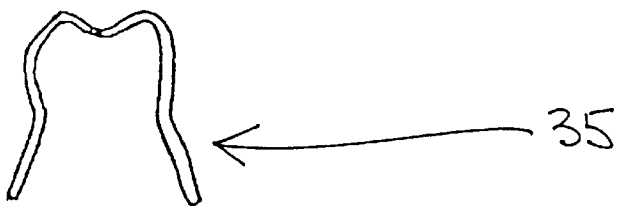
FIG. 44 is a cross-section view of the crown form taken along line a–a' in FIG. 43.

Referring to FIGS. 42, 43, & 44, the pontic fabrication process can employ a crown form 35 instead of the mold 32, such that mold formation steps would be eliminated, with polymer deposition and curing steps occurring identically in the manner described with regard to the wax mold process.

Custom-fabricating the pontic 36 using the ex situ method described above has been found to be advantageous over merely selecting a pontic from commercially available stock, because stock pontics will not chemically adhere to attachment portions or a bridge substructure, which are formed of composite material according to the present invention.

Figure 45:
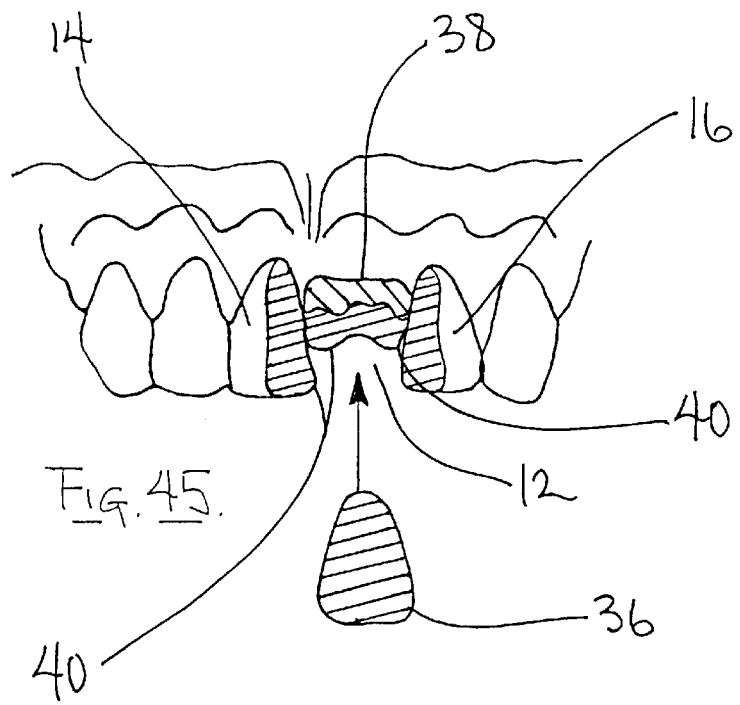
FIG. 45 is a front view of a dental arch similar to FIG. 3, additionally showing intended placement of pontic in the edentulous space of the dental arch, in accordance with the ex situ process and without using a gingival stent.
Figure 46:
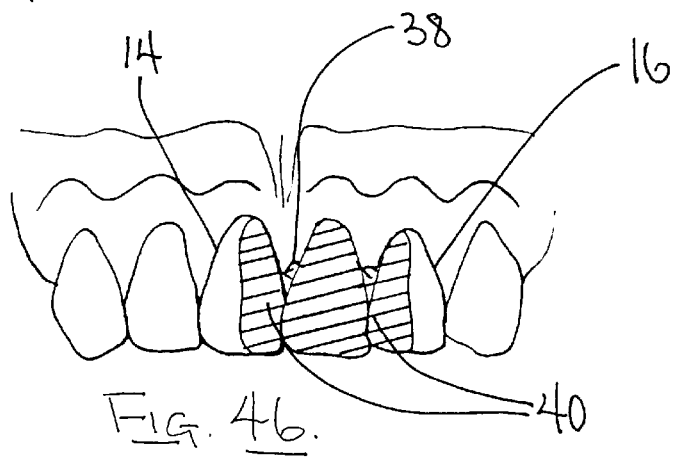
FIG. 46 is a front view similar to FIG. 45, except that it shows actual placement of the pontic in the edentulous space.
Figure 47:
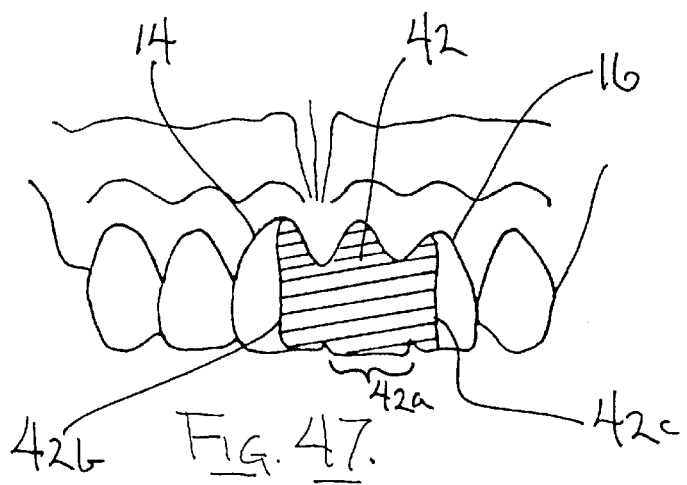
FIG. 47 is a front view similar to FIG. 45, except that it shows a completed bridge constructed in accordance with the ex situ process.

In FIGS. 46 & 47, the attachment surfaces of the abutment teeth 14, 16 have been prepared, and the gingival stent 20, if used (including leaf 26), inserted in the same manner as previously described with regard to the in situ process. Here, the completed pontic 36 is aligned with the edentulous space 12, as shown in FIG. 45. Next, an initial layer of composite material 38 is seen as having been applied between the first and second abutment teeth 14, 16, respectively. Layer 38 is then cured, whereafter a lamination of additional composite material 40 is applied between the abutment teeth; curing does not immediately follow; rather, the composite pontic 36 is first inserted into the uncured lamination 40, as seen in FIG. 46. Once this occurs, lamination 40 is cured. If desired, the gingival surface of composite pontic 36 may be serrated, or roughened, while partially cured to create more surface area with which to bond the pontic to one or more uncured composite laminations on the bridge substructure.

Referring to FIG. 47, successive additional laminations of composite material and curing thereof result in a completed dental bridge 42, including pontic portion 42a and attachment portions 42b, 42c. If desired, reinforcement material can be introduced in the manner described for the in situ process. The ex situ process is then completed by shaping and finishing the bridge 42 in the same manner as that described with regard to the in situ process.

It is therefore seen that a direct, immediate, light-cured direct composite dental bridge spanning one or more alveoli, with or without reinforcement, and constructed with one or more dental composites may be efficiently constructed in a manner which results in several advantages, namely: a) no tooth preparation by extensive enamel reduction, which prevents pulpal death and attendant complex endodontic treatment; b) often no need for anesthetic injections; c) no need for dental impressions in the in situ process; d) no need for temporary bridges; e) aesthetic input from the patient at the time of bridge lamination and completion; f) elimination of casting or porcelain errors within the laboratory; g) obviates errors in occlusion (bite) due to articulation errors and model inaccuracies; h) revolutionary "one-phase" material application; i) no laboratory procedures saving time, materials, and expense; j) no cementation of the bridge framework to the abutment teeth after the indirect construction of the bridge framework with the pontic; k) one appointment only for the patient; l) when non-metallic reinforcement materials are used, no metal corrosive activity or ionization, thus preventing metal ion bio-contamination; m) the bridge can be reinforced as appropriate; n) finishing errors can be easily corrected; and, o) the bridge will not need to be removed for repair or correction of shade, since all addition or shade changes may be made directly to the pontics in the existing direct composite bridge at any time in the future.

As the above description is merely exemplary in nature, being merely illustrative of the invention, many variations will become apparent to those of skill in the art. Such variations, however, are included within the spirit and scope of this invention as defined by the following appended claims.

I claim:

1. A method of constructing a dental bridge in situ, said dental bridge when completed occupying an edentulous space between a first abutment tooth and a second abutment tooth in a mouth of a patient, comprising the steps of:

applying an initial lamination of a dental composite material onto an attachment surface of the first abutment tooth, across the edentulous space, and onto an attachment surface of the second abutment tooth;

curing the initial lamination of the dental composite material;

applying additional laminations of the dental composite material onto an attachment surface of the first abutment tooth, across the edentulous space onto an attachment surface of the second abutment tooth, and in contact with at least one previously applied and cured lamination of the dental composite material; and curing each additional lamination of the dental composite material;

whereby a dental bridge is constructed entirely within the mouth of the patient.

2. A method of constructing a dental bridge in situ, said dental bridge when completed occupying an edentulous space between a first abutment tooth and a second abutment tooth in a mouth of a patient, comprising the steps of:

applying an initial lamination of a first type of dental composite material onto an attachment surface of the first abutment tooth, across the edentulous space, and onto an attachment surface of the second abutment tooth;

curing the initial lamination of the first type of dental composite material;

applying additional laminations of the first type of dental composite material onto an attachment surface of the first abutment tooth across the edentulous space onto an attachment surface of the second abutment tooth and in contact with at least one previously applied and cured lamination of the first type of dental composite material;

curing each additional lamination of the first type of dental composite material applying an initial lamination of a second type of dental composite material onto an attachment surface of the first abutment tooth, across the edentulous space, onto an attachment surface of the second abutment tooth, and in contact with at least one previously applied and cured lamination of the first type of dental composite;

curing the initial lamination of the second type of dental composite material;

applying additional laminations of the second type of dental composite material onto an attachment surface of the first abutment tooth across the edentulous space, onto an attachment surface of the second abutment tooth, and in contact with at least one previously applied and cured lamination of dental composite material; and curing each additional lamination of the second type of dental composite material;

whereby a dental bridge is constructed entirely within the mouth of the patient.

3. A method of constructing a dental bridge in situ with one or more integral pontics, said dental bridge when completed occupying an edentulous space between a first abutment tooth and a second abutment tooth in a mouth of a patient, comprising the steps of:

applying an initial lamination of a first type of dental composite material onto an attachment surface of the first abutment tooth, across the edentulous space, and onto an attachment surface of the second abutment tooth, curing the initial lamination of the first type of dental composite material;

applying additional laminations of the first type of dental composite material onto an attachment surface of the first abutment tooth, across the edentulous space, onto an attachment surface of the second abutment tooth, and in contact with at least one previously applied and cured lamination of the first type of dental composite material;

curing each additional lamination of the first type of dental composite material;

applying an initial lamination of a second type of dental composite material across a portion of the edentulous space, and in contact with at least one previously applied and cured lamination of the first type of dental composite;

curing the initial lamination of the second type of dental composite material;

applying additional laminations of the second type of dental composite material across a portion of the edentulous space, and in contact with at least one previously applied and cured lamination of dental composite material;

curing each additional lamination of the second type of dental composite material; and progressively shaping such additional laminations of dental composite material into one or more pontics;

whereby a dental bridge is constructed entirely within the mouth of the patient.

4. A method of constructing a dental bridge in situ with one or more integral pontics, said dental bridge when completed occupying an edentulous space between a first abutment tooth and a second abutment tooth in a mouth of a patient, comprising the steps of applying an initial lamination of a first type of dental composite material onto an attachment surface of the first abutment tooth, across the edentulous space, and onto an attachment surface of the second abutment tooth;

curing the initial lamination of the first type of dental composite material;

applying additional laminations of the first type of dental composite material onto an attachment surface of the first abutment tooth, across the edentulous space, onto an attachment surface of the second abutment tooth, and in contact with at least one previously applied and cured lamination of the first type of dental composite material;

curing each additional lamination of the first type of dental composite material;

applying an initial lamination of a second type of dental composite material across a portion of the edentulous space and in contact with at least one previously applied and cured lamination of the first type of dental composite;

curing the initial lamination of the second type of dental composite material;

applying additional laminations of the second type of dental composite material onto an attachment surface of the first abutment tooth, across the edentulous space, onto an attachment surface of the second abutment tooth, and in contact with at least one previously applied and cured lamination of dental composite material;

curing each additional lamination of the second type of dental composite material; and progressively shaping such additional laminations of dental composite material into one or more pontics.

whereby a dental bridge is constructed entirely within the mouth of the patient.

5. The method set forth in claims 1, 2, 3, or 4, further comprising the steps of:

prior to completion of half of the final height of the composite bridge, applying one or more additional laminations of composite in the edentulous area;

inserting into the one or more uncured laminations of composite in the edentulous area in proper occlusal or incisal position a pontic that was prepared outside the patient's mouth;

curing the laminations of composite; and completing the construction of the composite bridge.

6. The method set forth in claims 1, 2, 3, or 4, further comprising the steps of:

placing a layer of wax over a third tooth within a same dental arch as the first and second abutment teeth, thereby forming a wax mold of the third tooth;

removing said mold from the third tooth;

cooling said mold;

placing a layer of un-filled resin polymer within said mold;

curing said layer;

placing a layer of filled resin polymer within said mold;

curing said layer of filled resin polymer;

repeating said steps of placing a layer of filled resin polymer within said mold and of curing each such layer of filled resin polymer until a completed composite pontic is formed within said mold;

removing said completed composite pontic from said mold;

prior to completion of half of the final height of the composite bridge, applying one or more additional laminations of composite in the edentulous area;

inserting in proper occlusal or incisal position said completed pontic into the one or more uncured laminations of composite in the edentulous area;

curing the laminations of composite; and completing the construction of the composite bridge.

7. The method set forth in claims 2, 3, or 4, in which the second type of dental composite has a higher tensile, transverse, compressive, or shear strength than the first type of dental composite.

8. The method set forth in claims 2, 3, or 4, in which the second type of dental composite has a different modulus of elasticity than the first type of dental composite.

9. The method set forth in claims 2, 3, or 4, in which the second type of dental composite has a different modulus of elasticity than the first type of dental composite and is applied in the buccal, labial, incisal, or occlusal portions of one or more pontics in the composite bridge.

10. The method set forth in claims 2, 3, or 4, in which a third type of dental composite is applied, shaped, and cured in the buccal, labial, incisal, or occlusal portions of one or more pontics in the composite bridge.

11. The method set forth in claims 1, 2, 3, or 4, further comprising the steps of:

prior to construction or insertion of a pontic, as the case may be, in the composite bridge, applying one or more additional laminations of composite in the edentulous area;

inserting in the additional laminations reinforcing material selected from the group consisting of bondable reinforcement ribbon, metallic rods, non-metallic rods, foils, films, trusses, masts, and screens;

curing the laminations of composite, thereby securing the reinforcement material in the composite bridge;

applying one or more additional laminations of composite in the edentulous area;

curing the additional laminations of composite, thereby encasing the reinforcement material in the composite bridge; and completing the construction of the composite bridge.

12. The method set forth in claims 1, 2, 3, or 4, further comprising the steps of:

prior to the initial laminations of composite in an edentulous area that contains endodontic posts, reducing such posts so that the posts do not interfere with the placement of any material to be embedded in the composite bridge; and completing the construction of the composite bridge.

13. The method set forth in claims 1, 2, 3, or 4, further comprising the steps of:

prior to the initial laminations of composite in an edentulous area, inserting endodontic posts into the alveolar ridge of the edentulous area, dimensioning such posts so that the posts do not interfere with the placement of any material to be embedded in the composite bridge; and completing the construction of the composite bridge.

14. The method set forth in claims 1, 2, 3, or 4, further comprising the step of etching the attachment surfaces before the initial application of composite material.

15. The method set forth in claims 1, 2, 3, or 4, further comprising the step of contouring and finishing the composite bridge after curing of the last application of composite used in the composite bridge.

16. A dental bridge, said dental bridge when completed occupying an edentulous space between a first abutment tooth and a second abutment tooth in the mouth of a patient, comprising:

attachment portions of a single type of laminated dental composite that have faces that exactly match one or more attachment surfaces on the first abutment tooth and one or more attachment surfaces on the second abutment tooth in the mouth of the patient;

one or more composite pontics; and a laminated substructure of said single type of dental composite integral with the attachment portions and the one or more composite pontics.

17. A dental bridge, said dental bridge constructed without laboratory prepared attachment portions and when completed occupies an edentulous space between a first abutment tooth and a second abutment tooth in the mouth of a patient, comprising:

attachment portions of laminated dental composite that exactly match one or more attachment surfaces on the first abutment tooth and one or more attachment surfaces on the second abutment tooth;

one or more pontics, each of which pontics contain one or more types of dental composite; and a substructure of laminated dental composite integral with the attachment portions and the one or more composite pontics and that contains one or more types of dental composite.

18. A dental bridge, said dental bridge when completed occupying an edentulous space between a first abutment tooth and a second abutment tooth in the mouth of a patient, comprising:

attachment portions of dental composite, which attachment portions contain two or more types of dental composite and have faces that correspond to attachment surfaces on the first abutment tooth and to attachment surfaces on the second abutment tooth;

one or more pontics, each of which pontics contain one or more types of dental composite; and a substructure integral with the attachment portions and the one or more composite pontics and that contains one or more types of dental composite.

19. A dental bridge as set for in claims 16, 17, or 18, further comprising reinforcement materials embedded in the substructure of the bridge.

20. A dental bridge as set for in claims 16, 17, or 18, further comprising reinforcement materials embedded in the substructure of the bridge and selected from the group consisting of bondable reinforcement ribbon, metallic or non-metallic rods, metallic posts, non-metallic posts, foils, films, trusses, masts, and screens.

* * * * *